United States Patent
Groves et al.

(10) Patent No.: US 9,913,917 B2
(45) Date of Patent: Mar. 13, 2018

(54) BIOCOMPATIBLE FLUORESCENT METAL OXIDE NANOPARTICLES

(75) Inventors: Kevin Groves, Somerville, MA (US); Milind Rajopadhye, Westford, MA (US)

(73) Assignee: VisEn Medical, Inc., Waltham, MA (US)

( * ) Notice: Subject to any disclaimer, the term of this patent is extended or adjusted under 35 U.S.C. 154(b) by 1500 days.

(21) Appl. No.: 11/645,111

(22) Filed: Dec. 22, 2006

(65) Prior Publication Data

US 2008/0226562 A1  Sep. 18, 2008

Related U.S. Application Data

(60) Provisional application No. 60/753,805, filed on Dec. 22, 2005, provisional application No. 60/783,460, filed on Mar. 16, 2006.

(51) Int. Cl.
  *A61K 49/18* (2006.01)
  *A61K 49/00* (2006.01)
  *B82Y 5/00* (2011.01)

(52) U.S. Cl.
  CPC ...... *A61K 49/1866* (2013.01); *A61K 49/0002* (2013.01); *A61K 49/0032* (2013.01); *A61K 49/0056* (2013.01); *A61K 49/0093* (2013.01); *A61K 49/186* (2013.01); *A61K 49/1833* (2013.01); *B82Y 5/00* (2013.01)

(58) Field of Classification Search
  None
  See application file for complete search history.

(56) References Cited

U.S. PATENT DOCUMENTS

| | | | |
|---|---|---|---|
| 4,101,435 A | 7/1978 | Hasegawa et al. | |
| 4,219,335 A | 8/1980 | Ebersole | |
| 4,369,226 A | 1/1983 | Rembaum | |
| 4,438,239 A | 3/1984 | Rembaum et al. | |
| 4,452,773 A | 6/1984 | Molday | |
| 4,628,037 A * | 12/1986 | Chagnon et al. | 436/526 |
| 4,654,267 A | 3/1987 | Ugelstad et al. | |
| 4,981,977 A | 1/1991 | Southwick et al. | |
| 5,164,297 A | 11/1992 | Josephson et al. | |
| 5,204,457 A | 4/1993 | Maruno et al. | |
| 5,262,176 A | 11/1993 | Palmacci et al. | |
| 5,268,486 A | 12/1993 | Waggoner et al. | |

(Continued)

FOREIGN PATENT DOCUMENTS

| | | |
|---|---|---|
| CA | 2384429 A1 | 3/2001 |
| EP | 1065250 | 1/2001 |

(Continued)

OTHER PUBLICATIONS

Banks et al., Bioconjugate Chem, 6(4), p. 447-458, 1995.*
(Continued)

*Primary Examiner* — Nissa M Westerberg
(74) *Attorney, Agent, or Firm* — Goodwin Procter LLP

(57) ABSTRACT

The invention relates to highly fluorescent metal oxide nanoparticles to which biomolecules and other compounds can be chemically linked to form biocompatible, stable optical imaging agents for in vitro and in vivo applications. The fluorescent metal oxide nanoparticles may also be used for magnetic resonance imaging (MRI), thus providing a multi modality imaging agent.

36 Claims, 6 Drawing Sheets

(56) References Cited

U.S. PATENT DOCUMENTS

| | | | |
|---|---|---|---|
| 5,395,688 A | 3/1995 | Wang et al. | |
| 5,424,419 A | 6/1995 | Hasegawa et al. | |
| 5,445,970 A | 8/1995 | Rohr | |
| 5,478,576 A | 12/1995 | Jung et al. | |
| 5,486,616 A | 1/1996 | Waggoner et al. | |
| 5,512,439 A | 4/1996 | Hornes et al. | |
| 5,539,658 A | 7/1996 | McCullough | |
| 5,569,587 A | 10/1996 | Waggoner | |
| 5,569,766 A | 10/1996 | Waggoner et al. | |
| 5,593,658 A | 1/1997 | Bogdanov et al. | |
| 5,627,027 A | 5/1997 | Waggoner | |
| 5,808,044 A | 9/1998 | Brush et al. | |
| 5,877,310 A | 3/1999 | Reddington et al. | |
| 5,981,507 A | 11/1999 | Josephson et al. | |
| 6,002,003 A | 12/1999 | Shen et al. | |
| 6,004,536 A | 12/1999 | Leung et al. | |
| 6,008,373 A | 12/1999 | Waggoner et al. | |
| 6,043,025 A | 3/2000 | Minden et al. | |
| 6,046,585 A | 4/2000 | Simmonds | |
| 6,074,884 A | 6/2000 | Siiman et al. | |
| 6,083,485 A | 7/2000 | Licha et al. | |
| 6,083,486 A | 7/2000 | Weissleder et al. | |
| 6,120,856 A | 9/2000 | Liberti et al. | |
| 6,127,134 A | 10/2000 | Minden et al. | |
| 6,130,094 A | 10/2000 | Waggoner et al. | |
| 6,133,047 A | 10/2000 | Elaissari et al. | |
| 6,133,445 A | 10/2000 | Waggoner et al. | |
| 6,136,612 A | 10/2000 | Della Ciana et al. | |
| 6,248,539 B1 | 6/2001 | Ghadiri et al. | |
| 6,258,340 B1 | 7/2001 | Licha et al. | |
| 6,274,121 B1 | 8/2001 | Pilgrimm | |
| 6,275,031 B1 | 8/2001 | Simmonds | |
| 6,448,008 B1 | 9/2002 | Caputo et al. | |
| 6,503,762 B1 | 1/2003 | Yamauchi et al. | |
| 6,534,041 B1 | 3/2003 | Licha et al. | |
| 6,548,264 B1 | 4/2003 | Tan et al. | |
| 6,592,847 B1 | 7/2003 | Weissleder et al. | |
| 6,615,063 B1 | 9/2003 | Ntziachristos et al. | |
| 6,720,177 B2 | 4/2004 | Ghadiri et al. | |
| 6,720,351 B2 | 4/2004 | Bertinato et al. | |
| 6,734,000 B2 | 5/2004 | Chin et al. | |
| 6,740,755 B2 | 5/2004 | Caputo et al. | |
| 6,747,159 B2 | 6/2004 | Caputo et al. | |
| 6,767,635 B1 | 7/2004 | Bahr et al. | |
| 6,869,593 B2 | 3/2005 | Frangioni | |
| 6,913,743 B2 | 7/2005 | Licha et al. | |
| 6,926,885 B2 | 8/2005 | Licha et al. | |
| 6,949,572 B2 | 9/2005 | Bertinato et al. | |
| 7,025,949 B2 | 4/2006 | Licha et al. | |
| 7,374,746 B2 | 5/2008 | Frangioni | |
| 7,445,767 B2 | 11/2008 | Licha et al. | |
| 7,655,217 B2 | 2/2010 | Licha et al. | |
| 7,947,256 B2 | 5/2011 | Rajopadhye et al. | |
| 8,173,819 B2 | 5/2012 | Rajopadhye et al. | |
| 8,221,721 B2 | 7/2012 | Narayanan | |
| 8,420,055 B2 | 4/2013 | Gaw et al. | |
| 8,455,651 B2 | 6/2013 | Rajopadhye et al. | |
| 8,486,373 B2 | 7/2013 | Weissleder et al. | |
| 8,685,370 B2 | 4/2014 | Rajopadhye et al. | |
| 8,771,646 B2 | 7/2014 | Rajopadhye et al. | |
| 8,815,214 B2 | 8/2014 | Rajopadhye et al. | |
| 8,864,821 B2 | 10/2014 | Jaffer et al. | |
| 2003/0092029 A1* | 5/2003 | Josephson et al. | 435/6 |
| 2003/0124194 A1* | 7/2003 | Gaw et al. | 424/491 |
| 2003/0206859 A1 | 11/2003 | Chen et al. | |
| 2005/0130167 A1 | 6/2005 | Bao et al. | |
| 2005/0169843 A1 | 8/2005 | Weissleder et al. | |
| 2005/0171434 A1 | 8/2005 | Madden et al. | |
| 2005/0214221 A1 | 9/2005 | Poss et al. | |
| 2006/0169843 A1 | 8/2006 | Barrs et al. | |
| 2006/0275775 A1 | 12/2006 | Weissleder et al. | |
| 2008/0102036 A1 | 5/2008 | Poss et al. | |
| 2008/0226562 A1 | 9/2008 | Groves et al. | |
| 2009/0068115 A1 | 3/2009 | Gaw et al. | |
| 2009/0130024 A1 | 5/2009 | Narayanan et al. | |
| 2010/0074847 A1 | 3/2010 | Madden et al. | |
| 2010/0166659 A1 | 7/2010 | Licha et al. | |
| 2010/0172841 A1 | 7/2010 | Peterson et al. | |
| 2010/0189657 A1 | 7/2010 | Weissleder et al. | |
| 2011/0171136 A1 | 7/2011 | Poss et al. | |
| 2012/0321563 A1 | 12/2012 | Groves et al. | |
| 2014/0050662 A1 | 2/2014 | Ho | |
| 2014/0314677 A1 | 10/2014 | Groves et al. | |
| 2014/0348746 A1 | 11/2014 | Narayanan | |

FOREIGN PATENT DOCUMENTS

| | | |
|---|---|---|
| EP | 1787659 A1 | 5/2007 |
| EP | 1787661 A1 | 5/2007 |
| WO | WO-1997/021452 A2 | 6/1997 |
| WO | WO-1997/040104 | 10/1997 |
| WO | WO-1999/051702 | 10/1999 |
| WO | WO-2000/061191 A2 | 10/2000 |
| WO | WO 2001/019405 A2 | 3/2001 |
| WO | WO-2001/020338 A1 | 3/2001 |
| WO | WO-2001/021624 | 3/2001 |
| WO | WO-2002/098364 A2 | 12/2002 |
| WO | WO-2003/07579 A2 | 1/2003 |
| WO | WO-2003/057175 A2 | 7/2003 |
| WO | WO-2003/079015 | 9/2003 |
| WO | WO-2003/102558 A1 | 12/2003 |
| WO | WO-2004/026344 A1 | 4/2004 |
| WO | WO-2004/083902 | 9/2004 |
| WO | WO-2004/108902 | 12/2004 |
| WO | WO-2005/017539 | 2/2005 |
| WO | WO-2006/010083 A2 | 1/2006 |
| WO | WO 2006/028129 A1 | 3/2006 |
| WO | WO-2007/021946 A2 | 2/2007 |
| WO | WO-2007/028037 | 3/2007 |
| WO | WO-2007/028118 | 3/2007 |
| WO | WO-2007/028163 | 3/2007 |
| WO | WO-2007/136413 | 11/2007 |

OTHER PUBLICATIONS van Kerkhof et al., Biosensors & Bioelectronics 10, p. 269-282, 1995.*
Xu et al., J Biomed Mater Res 66A: 870-879, 2003.*
Frangioni, Curr Op Chem Bio 7, p. 626-634, 2003.*
Arbab et al. Blood 104, p. 1217-1223, 2004.*
Becker et al. Bioconjugate Chemistry, 15(4), p. 699-709, 2004.*
MacKay and Szoka, Journal of dispersion science and technology 24 (3), p. 465-473, 2003.*
Rohatgi, K. K., and G. S. Singhal. "Nature of bonding in dye aggregates."The Journal of Physical Chemistry 70.6 (1966): 1695-1701.*
Eliyahu et al. (2005) "Polymers for DNA Delivery," *Molecules* 10: 24-64.
Delie et al. (2005) "Polymeric Particulates to Improve Oral Bioavailability of Peptide Drugs," *Molecules* 10: 65-80.
Park et al. (2005) "Biodegradable Polymers for Microencapsulation of Drugs," *Molecules* 10: 146-161.
Pinaud et al. (2006) "Advances in Fluorescence Imaging with Quantum Dot Bio-probes," *Biomaterials* 27(9): 1679-1687.
McNeil, S. (2005) "Nanotechnology for the Biologist," *Journal of Leukocyte Biology* 78:585-594.
Yih et al. (2006) "Engineered Nanoparticles as Precise Drug Delivery Systems" *Journal of Cellular Biochemistry* 97: 1184-1190.
Mohanraj et al. (2006) "Nanoparticles—A Review," *Tropical Journal of Pharmaceutical Research* 5(1): 561-573.
Brigger et al. (2002) "Nanoparticles in Cancer Therapy and Diagnosis," *Advanced Drug Delivery Reviews* 54: 631-651.
Gupta et al. (2005) "Synthesis and Surface Engineering of Iron Oxide Nanoparticles for Biomedical Applications," *Biomaterials* 26:3995-4021.
Achilefu et al. (2000) "Novel Receptor-Targeted Fluorescent Contrast Agents for In Vivo Tumor Imaging," *Invest. Radiol.* 35:479-485.
Alauddin et al. (2003) "Receptor Mediated Uptake of a Radiolabeled Contrast Agent Sensitive to Beta-Galectosidase Activity," *Nuclear Medicine and Biology* 30:261-265.

(56) References Cited

OTHER PUBLICATIONS

Alfano et al. (1997) "Advances in optical imaging of biomedical media," *Ann. NY Acad. Sci.* 820:248-271.
Allen et al. (2004) "Magnetic Resonance Contrast Agents for Medical and Molecular Imaging," *Metal Ions Biol. Syst.* 42:1-38.
Ballou et al. (1997) "Tumor Detection and Visualization Using Cyanine Fluorochrome-Labeled Antibodies," *Biotechnol. Prog.* 13:649-658.
Becker et al. (2001) Receptor-Targeted Optical Imaging of Tumors with Near-Infrared Fluorescent Ligands, *Nature Biotech.* 19:327-331.
Bremer et al. "In Vivo Molecular Target Assessment of Matrix Metalloproteinase Inhibition," (2001) *Nature Med.* 7:743-748.
Bugai et al. (2001) "Novel Fluorescent Contract Agents for Optical Imaging of in vivo Tumor Based on a Receptor-Targeted Dye-Peptide Conjugate Platform," *J. Biomed. Opt.* 6:122-133.
Chemla et al. (2000) "Ultrasensitive Magnetic Biosensor for Homogeneous Immunoassay," *PNAS* 97: 14268-14272.
Chen et al. (2003) "Sodium Chloride Modified Silica Nanoparticles as a Non-Viral Vector with a High Efficiency of DNA Transfer into Cells," *Current Gene Therapy* 3: 273-279.
Cunin et al. (2002) "Biomolecular Screening with Encoded Porous-Silicon Photonic Crystals," *Nature Materials* 1: 39-41.
Derfus et al. (2004) "Probing the Cytotoxicity of Semiconductor Quantum Dots " *Nano Lett.* 4:11-18.
Examination Report of the European Patent Office for EP 03705645.4, dated Sep. 25, 2007, 3 pages.
Examination Report of the European Patent Office for EP 03705645.4, dated May 25, 2009, 4 pages.
Goetze et al. (2002) "Biocompatible Magnetic Core/Shell Nanoparticles," *Journal of Magnetism and Magnetic Materials* 252:399-402.
Gupta and Gupta (2005) "Synthesis and Surface Engineering and Iron Oxide Nanoparticles for Biomedical Applications," *Biomaterials* 26:3995-4021.
Högemann et al. (2000) Improvement of MRI Probes to Allow Efficient Detection of Gene Expression,: *Bioconjugate Chem.* 11:941-946.
Högemann et al. (2002) "High Throughput Magnetic Resonance Imaging for Evaluating Targeted Nanoparticle Probes," *Bioconjugate Chem.* 13(1):116-121.
Hüber et al. (1998) "Fluorescently Detectable Magnetic Resonance Imaging Agents," *Bioconjugate Chem.* 9(2):242-249.
International Preliminary Examination Report for PCT/US2003/000051, dated Nov. 28, 2003, 3 pages.
International Search Report of the International Searching Authority for PCT/US2006/049222 dated Sep. 8, 2008, 10 pages.
International Search Report of the International Searching Authority for PCT/US2003/000051 dated Jul. 29, 2003, 1 page.
Jaffer et al. (2006) "Molecular imaging of myocardial infarction," *J. Mol. Cell. Cardiology.* 41(6):921-933.
Josephson et al. (2002) "Near-infrared fluorescent nanoparticles as combined MR/optical imaging probes," *Bioconjugate Chem.* 13(3):554-560.
Josephson et al. (1996) "Antiviral Activity of a Conjugate of Adenine-9-β-D-Arabinofuranoside 5"-Monophosphate and a 9 kDa Fragment of Arabinogalactan," *Antiviral Therapy* 1:147-156.
Josephson et al. (1999) "High-efficiency intracellular magnetic labeling with novel superparamagnetic-Tat peptide conjugates," *Bioconjugate Chem.* 10(2):186-191.
Josephson et al. (2001) "Magnetic Nanosensors for the Detection of Oligonucleotide Sequences," *Angew. Chem. Int. Ed*. 40: 3204-3206.
Kim et al. (2003) "Type-II Quantum Dots: CdTe/CdSe(core/shell) and CdSe/ZnTe(core/shell) Heterostructures," *J. Am. Chem. Soc.* 125:11466-11467.
Kircher et al. (2003) "A multimodal nanoparticle for preoperative magnetic resonance imaging and intraoperative optical brain tumor delineation," *Cancer Research* 63:8122-8125.
Kircher et al. (2004) "A Dual Fluorochrome Probe for Imaging Proteases " *Bioconiugate Chem.* 15: 242-248.

Koo et al. (2006) "Brain cancer diagnosis and therapy with nanoplatforms " *Adv. Drug Delivery Reviews* 58(14):1556-1577.
Kreuter (1996) "Nanoparticles and Microparticles for Drug and Vaccine Delivery " *Journal of Anatomy* 189: 503-505.
Leamon et al. (2001) "Folate-Mediated Targeting: From Diagnostics to Drug and Gene Delivery," *Drug Discovery Today* 1(6): 44-51.
Meade et al. (2003) "New Magnetic Resonance Contrast Agents as Biochemical Reporters," *Curr Opin Neurobiol.* 13(5):597-602.
Medarova et al. (2005) "In vivo imaging of tumor response to therapy using a dual-modality imaging strategy," *Int. J. Cancer* 118(11):2796-2802.
Neri et al. (1997) "Targeting by Affinity-Matured Recombinant Antibody Fragments of an Angiogenesis Associated Fibronectin Isoform," *Nature Biotech.* 15:1271-1275.
Ntziachristos et al. (2000) "Concurrent MRI and Diffuse Optical Tomography of Breast After Indocyanine Green Enhancement," *PNAS* 97: 2767-2772.
Ozmen et al. (2000) "Infrared fluorescence sensing of submicromolar calcium: pushing the limits of photoinduced electron transfer," *Tetrahedron Letters*, 41:9185-9188.
Pardoe et al. (2001) "Structural and Magnetic Properties of Nanoscale Iron Oxide Particles Synthesized in the Presence of Dextran or Polyvinyl Alcohol," *Journal of Magnetism and Magnetic Materials* 225: 41-46.
Qhobosheane et al. (2001) "Biochemically Functionalized Silica Nanoparticles," *Analyst* 126: 1274-1278.
Reynolds et al. (1977) "Stable Heptamethine Pyrylium Dyes that Absorb in the Infrared," *J. Org. Chem.* 22(5) 885-888.
Reynolds et al. (2005) "Protamine as an Efficient Membrane-Translocating Peptide," *Bioconiugate Chem.* 16(5):1240-1245.
Satomura et al. (1984) "Kinetics of Human Pancreatic and Salivary α-Amylases with Carboxymethylamyloses as Substrates " *Clinica Chimica Acta* 138: 21-29.
Schellenberger et al. (2004) "Magneto/Optical Annexin V, a Multimodal Protein " *Bioconjugate Chemistry* 15:1062-1067.
Schütt et al. (1997) "Applications of Magnetic Targeting in Diagnosis and Therapy—Possibilities and Limitations: A Mini-Review," *Hybridoma* 16: 109-117.
Summons to attend oral proceedings issued by the European Patent Office for EP 03705645.4, dated Mar. 4, 2011, 5 pages.
Sun et al. (2006) ""Clickable" Nanoparticles for Targeted Imaging," *Mol. Imaging* 5(2):122-128.
Supplementary Partial European Search Report for EP 03705645.4, PCT/2003/000051, dated Jun. 8, 2006, 4 pages.
Santra et al. (2001) "Conjugation of Biomolecules with Luminophore-Doped Silica Nanoparticles for Photostable Biomarkers," *Analytical Chemistry* 73(20): 4988-4993.
Tearney et al. (1996) "Catheter-Based Optical Imaging of a Human Coronary Artery," *Circulation* 94:3013.
Tsourkas et al. (2005) "In Vivo imaging of activated endothelium using an anti-VCAM-1 magnetooptical probe," *Bioconjugate Chem.* 16(3): 576-581.
Tyagi et al. (1998) "Multicolor Molecular Beacons for Allele Discrimination," *Nat. Biotechnol.* 16:49-53.
Tyagi et al. (2000) "Wavelength-Shifting Molecular Beacons," *Nat. Biotechnol.* 18:1191-1196.
Veiseh et al. (2005) "Optical and MRI multifunctional nanoprobe for targeting gliomas " *Nano Letters* 5(6):1003-1008.
Weissleder et al. (1999) "In vivo imaging of tumors with protease-activated near-infrared fluorescent probes," *Nature Biotech.* 17:375-378.
Winter et al. (2003) "Molecular Imaging of Angiogenesis in Early-Stage Atherosclerosis With $\alpha_v\beta_3$-Integrin-Targeted Nanoparticles," *Circulation* 108:2270-2274.
Winter et al. (2003) "Molecular Imaging of Angiogenesis in Nascent Vx-2 Rabbit Tumors Using a Novel $\alpha_v\beta_3$-targeted Nanoparticle and 1.5 Tesla Magnetic Resonance Imaging," *Cancer Research* 63:5838-5843.
Written Opinion of the International Searching Authority for PCT/US2006/049222, dated Sep. 8, 2008, 10 pages.
Wunderbaldinger et al. (2002) "Tat Peptide Directs Enhanced Clearance and Hepatic Permeability of Magnetic Nanoparticles " *Bioconiugate Chem.* 13(2):264-268.

(56) References Cited

OTHER PUBLICATIONS

Zhang et al. (2005) "Gadolinium Meets Medicinal Chemistry: MRI Contrast Agent Development" *Curr. Med. Chem.* 12(7):751-778.

Genin et al. ""Hyper-bright" Near-Infrared Emitting Fluorescent Organic Nanoparticles for Single Particle Tracking" Adv. Mater. 2014, 26, 2258-2261.

Lin et al. "Novel Near-Infrared Cyanine Fluorochromes: Synthesis, Properties, and Bioconjugation" Bioconjugate Chem. 2002, 13, 605-610.

Mahmood et al. "Near-infrared optical imaging of proteases in cancer" Mol Cancer Ther. May 2003;2(5):489-96.

Reynolds et al. "Method of Determining Nanoparticle Core Weight" Anal. Chem. 2005, 77, 814-817.

Mishra et al. "Cyanines during the 1990s: A Review" Chem. Rev. 2000, 100, 1973-2011.

Renikuntla et al. "Improved Photostability and Fluorescence Properties through Polyfluorination of a Cyanine Dye" Org Lett. Mar. 18, 2004;6(6):909-12.

Schobel et al. "Mechanisms of Fluroescence Quenching in Donor-Acceptor Labeled Antibody-Antigen Conjugates" Journal of Fluorescence, vol. 10, No. 2, 2000.

Weissleder et al. "In vivo imaging of tumors with proteaseactivated near-infrared fluorescent probes" Nature Biotechnology vol. Apr. 17, 1999 375-378.

West et al. "The Dimeric State of Cyanine Dyes" The Journal of Physical Chemistry, vol. 69, No. 6 Jun. 1965 1894-1903.

ThermoFisher Scientific Molecular Probes Handbook "Fluorescence Fundamentals" (2010), accessed online Mar. 18, 2016 at <https://www.thermofisher.com/us/en/home/references/molecular-probes-the-handbook/introduction-to-fluorescence-techniques.html>.

Boas et al. "Scattering of diffuse photon density waves by spherical inhomogeneities within turbid media: analytic solution and applications" Proc Natl Acad Sci U S A. May 24, 1994;91(11):4887-91.

Alexander, "Lasers investigated as diagnostic tools for breast cancer" 1991, J. Clin Laser Med. Surg, 9:416-418.

Nziachristos, "Fluorescence molecular tomography resolves protease activity in vivo" 2002, Nature Med., 8:757-760.

\* cited by examiner

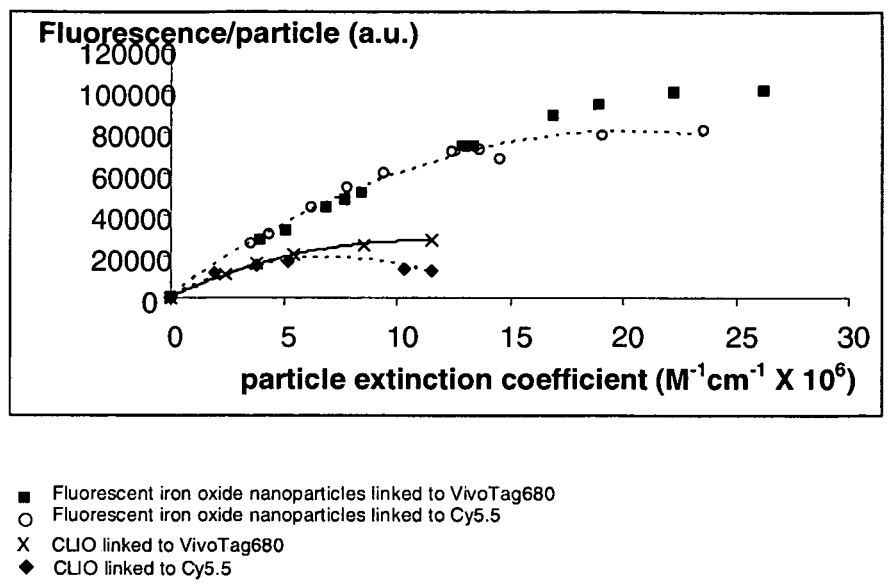
- ■ Fluorescent iron oxide nanoparticles linked to VivoTag680
- ○ Fluorescent iron oxide nanoparticles linked to Cy5.5
- X CLIO linked to VivoTag680
- ◆ CLIO linked to Cy5.5
FIG. 16
FIG 17
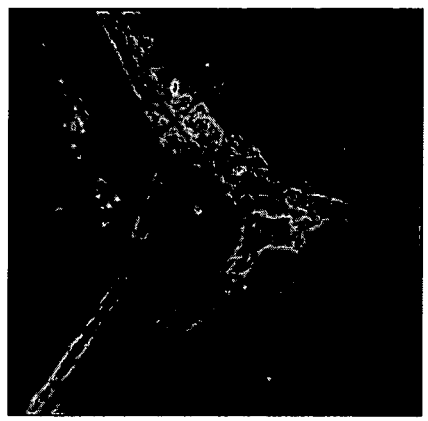

```
                        SEQUENCE LISTING

<160> NUMBER OF SEQ ID NOS: 14

<210> SEQ ID NO 1
<211> LENGTH: 7
<212> TYPE: PRT
<213> ORGANISM: Artificial Sequence
<220> FEATURE:
<223> OTHER INFORMATION: chemically synthesized

<400> SEQUENCE: 1

Ile Pro Leu Val Leu Pro Leu
1               5

<210> SEQ ID NO 2
<211> LENGTH: 7
<212> TYPE: PRT
<213> ORGANISM: Artificial Sequence
<220> FEATURE:
<223> OTHER INFORMATION: chemically synthesized

<400> SEQUENCE: 2

Ser Pro Pro Thr Gly Ile Asn
1               5

<210> SEQ ID NO 3
<211> LENGTH: 7
<212> TYPE: PRT
<213> ORGANISM: Artificial Sequence
<220> FEATURE:
<223> OTHER INFORMATION: chemically synthesized

<400> SEQUENCE: 3

Val His Pro Lys Gln His Arg
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: chemically synthesized

<400> SEQUENCE: 4

Val His Pro Lys Gln His Arg
1               5

<210> SEQ ID NO 5
<211> LENGTH: 18
<212> TYPE: PRT
<213> ORGANISM: Artificial Sequence
<220> FEATURE:
<223> OTHER INFORMATION: chemically synthesized

<400> SEQUENCE: 5

Cys Asp Ser Asp Ser Asp Ile Thr Trp Asp Gln Leu Trp Asp Asp Leu
1               5                   10                  15

Met Lys

<210> SEQ ID NO 6
<211> LENGTH: 9
<212> TYPE: PRT
<213> ORGANISM: Artificial Sequence
<220> FEATURE:
<223> OTHER INFORMATION: chemically synthesized

<400> SEQUENCE: 6

Arg Arg Arg Arg Gly Arg Arg Arg Arg
1               5

<210> SEQ ID NO 7
<211> LENGTH: 11
<212> TYPE: PRT
<213> ORGANISM: Artificial Sequence
<220> FEATURE:
<223> OTHER INFORMATION: chemically synthesized

<400> SEQUENCE: 7

Arg Arg Arg Arg Gly Arg Arg Arg Arg Gly Cys
1               5                   10

<210> SEQ ID NO 8
<211> LENGTH: 8
<212> TYPE: PRT
<213> ORGANISM: Artificial Sequence
<220> FEATURE:
<223> OTHER INFORMATION: chemically synthesized

<400> SEQUENCE: 8

Arg Arg Arg Arg Arg Arg Arg Cys
1               5

<210> SEQ ID NO 9
<211> LENGTH: 8
<212> TYPE: PRT
<213> ORGANISM: Artificial Sequence
<220> FEATURE:
<223> OTHER INFORMATION: chemically synthesized

<400> SEQUENCE: 9

Arg Arg Arg Arg Arg Arg Arg Cys
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: chemically synthesized

<400> SEQUENCE: 10

Arg Gly Asp Phe Cys
1               5

<210> SEQ ID NO 11
<211> LENGTH: 4
<212> TYPE: PRT
<213> ORGANISM: Artificial Sequence
<220> FEATURE:
<223> OTHER INFORMATION: chemically synthesized

<400> SEQUENCE: 11

Arg Gly Asp Ser
1

<210> SEQ ID NO 12
<211> LENGTH: 5
<212> TYPE: PRT
<213> ORGANISM: Artificial Sequence
<220> FEATURE:
<223> OTHER INFORMATION: chemically synthesized

<400> SEQUENCE: 12

Arg Gly Asp Phe Lys
1               5

<210> SEQ ID NO 13
<211> LENGTH: 9
<212> TYPE: PRT
<213> ORGANISM: Artificial Sequence
<220> FEATURE:
<223> OTHER INFORMATION: chemically synthesized

<400> SEQUENCE: 13

Gly Pro Leu Gly Val Arg Gly Gly Cys
1               5

<210> SEQ ID NO 14
<211> LENGTH: 13
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (11)..(11)
<223> OTHER INFORMATION: FITC (Fluorescent Dye)

<400> SEQUENCE: 14

Val His Pro Lys Gln His Arg Gly Gly Ser Lys Gly Cys
1               5                   10
```

BIOCOMPATIBLE FLUORESCENT METAL OXIDE NANOPARTICLES

RELATED APPLICATIONS

This application claims the benefit and priority to U.S. Provisional Patent Application Ser. No. 60/753,805, filed Dec. 22, 2005, and U.S. Provisional Patent Application Ser. No. 60/783,460, filed Mar. 16, 2006, the disclosures of which are incorporated by reference herein.

GOVERNMENT SUPPORT

The invention was supported, in whole or in part, by grant 1 R44RR020233-01 from the National Institutes of Health. The Government has certain rights in the invention.

BACKGROUND

Current approaches to the assessment of molecular endpoints in disease usually require tissue and blood sampling, surgery, and in the case of experimental animals, sacrifice at different time points. Despite improvement in noninvasive imaging, more sensitive and specific imaging agents and methods are urgently needed. Imaging techniques capable of visualizing specific molecular targets and/or entire pathways would significantly enhance our ability to diagnose and assess treatment efficacy of therapeutic interventions for many different disease states. Unfortunately, most current imaging techniques report primarily on anatomical or physiological information (e.g., magnetic resonance imaging (MRI), computed tomography (CT), ultrasound). Newer modalities such as optical imaging, especially when combined with traditional imaging modalities such as MRI and new molecular imaging probes have the potential to revolutionize the way disease is detected, treated, and monitored.

Molecular imaging is a new field in the imaging sciences that transcends the traditional boundaries of imaging structure or physiology and has the potential to revolutionize current research and clinical practices towards real molecular medicine. The common paradigm for molecular imaging involves the use of a "molecular" probe or agent that selectively targets a particular gene, protein, receptor or a cellular function, with the absence, presence or level of the specific target being indicative of a particular disease state.

Specifically, optical imaging offers several strong performance attributes that make it a truly powerful molecular imaging approach, both in the research and clinical settings. Specifically, optical imaging is fast, safe, cost effective and highly sensitive. Scan times are on the order of seconds to minutes, there is no ionizing radiation, and the imaging systems are relatively simple to use. In addition, optical probes can be designed as dynamic molecular imaging agents that can alter their reporting profiles in vivo to provide molecular and functional information in real time. In order to achieve maximum penetration and sensitivity in vivo, the choice for most optical imaging in biological systems is within the red and near-infrared (NIR) spectral region (600-900 nm), although other wavelengths in the visible region can also be used. In the NIR wavelength range, absorption by physiologically abundant absorbers such as hemoglobin or water is minimized.

Many different types of optical imaging probes have been developed including (1) probes that become activated after target contact (e.g., binding or interaction) (Weissleder et al., *Nature Biotech.*, 17:375-378, 1999; Bremer et al., *Nature Med.*, 7:743-748, 2001; Meade, Conti et al., *Nuclear Medicine and Biology*, 30:261-265, 2003), (2) wavelength shifting beacons (Tyagi et al., *Nat. Biotechnol.*, 18:1191-1196, 2000), (3) multicolor fluorescence probes (Tyagi et al., *Nat. Biotechnol.*, 16:49-53, 1998), (4) probes that have high binding affinity to targets, i.e., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001; Ballou et al. *Biotechnol. Prog.* 13:649-658, 1997; and Neri et al., *Nature Biotech.* 15:1271-1275, 1997), and (5) fluorescent semiconductor nanoparticles based probes (i.e., Quantum Dots Bawendi et al., *J. Am. Chem. Soc.*, 125: 11466-11467, 2003).

MRI also has demonstrated potential for molecular imaging. A number of targeted MRI agents have also been developed for molecular imaging applications including (1) metal oxide magnetic nanoparticles (Gupta and Gupta, *Biomaterials*, 26:3995-4021, 2005; Weissleder, et al., *Bioconjugate Chem.*, 13(1), 116-121, 2002; Weissleder, et al., *Bioconjugate Chem.*, 13(2): 264-268, 2002; Josephson, et al., *Bioconjugate Chem.*, 15(5):1062-1067, 2004; Josephson and Gaw, U.S. Patent Application Publication No. 2003/0124194), (2) emulsion "particles" consisting of a perfluorocarbon core surrounded by a lipid monolayer that are derivatized with targeting ligands and chelated gadolinium (Wickline et al., *Circulation*, 108: 2270-2274, 2003; Lanza, et al., *Cancer Research*, 63: 5838-5843, 2003); (3) probes that have high binding affinity to targets, i.e., that remain within a target region while non-specific probes are cleared from the body (McMurry et al., *Curr Med Chem*, 12(7): 751-78, 2005, and (4) probes that become activated after target contact (*Curr Opin Neurobiol.* 13(5): 597-602 2003).

In many research and clinical imaging settings it is desirable to have the ability to combine or make use of both high resolution anatomical and molecular information, provided by imaging techniques such as MRI, and molecular/functional information, provided by optical imaging approaches. Recent work in both clinical and pre-clinical imaging has integrated several modalities within a single system to great benefit compared with single-modality imaging systems and multi-modality imaging probes have been described (Meade et al., *Bioconjugate Chem.*, 9(2): 242-249, 1998; Meade and Allen, *Metal Ions Biol. Syst.*, 42: 1-38, 2004; Josephson et al., *Bioconjugate Chem.*, 13(3); 554-560, 2002; Josephson et al., *Bioconjugate Chem.*, 15(5); 1062-1067, 2004; Nie et al., U.S. Patent Appl. 2005/0130167; Hancu et al., WO2004026344).

To date however, the development of optical, MRI, and combined optical/MRI agents for molecular imaging applications has been limited by: 1) delivery barriers standing between molecularly targeted agents and their intended molecular target, 2) the fact that many monovalent ligands (antibodies, proteins, peptides) lack the affinity needed for efficient agent targeting, 3) limited target to background ratio due to sensitivity issues related to the signal strength of the individual agent (e.g., fluorescence or fluorescent brightness) of the individual agent, especially with regards deep tissue imaging (for optical agents) and low target abundance (MRI and optical agents), and 4) the limited biocompatibility and stability of some MRI (Palmacci and Josephson, U.S. Pat. No. 5,262,176) and optical agents (Bhatia et al., *Nano Lett.* 4: 11-18, 2004).

Thus, there is a need for biocompatible optical molecular imaging agents that can be specifically directed to a variety of molecular targets and provide high levels of sensitivity. In particular, there is a need for biocompatible multi-modality molecular imaging agents for in vivo imaging applications including in animals and in humans for disease detection, monitoring and assessing drug activities and therapeutic effects.

SUMMARY OF THE INVENTION

The present invention provides fluorescent metal oxide nanoparticles that are exceptionally fluorescent or have very high fluorescent brightness and can be used in a variety of in vitro and vivo applications. The fluorescent metal oxide nanoparticles are particularly useful as imaging agents that can be used for in vivo imaging. The fluorescent metal oxide nanoparticles may also have magnetic properties and, therefore, can be used for MRI, thus providing a multi-modality imaging agent.

Specifically, the design of the agents of the present invention provide fluorescent metal oxide nanoparticles with one or more of the following features: (1) a polymer coating suitable for attaching a plurality of fluorochromes thereby achieving large extinction coefficients (in excess of 1,000,000 $M^{-1}cm^{-1}$), (2) a non-crosslinked polymer coating suitable for attaching from about 10 to about 300 fluorochromes per particle, (3) a polymer coating suitable for attaching a plurality of fluorochromes in a manner that does not significantly compromise the quantum yield of the fluorochromes (e.g., the nanoparticles retain at least 50% of the fluorescent signal that is created by substantially the same number of free fluorochromes when tested under the same conditions), and (4) a polymer coating that is amenable to efficient chemical linking of biomolecules with retention of their biological properties to yield molecular imaging agents. The fluorescent metal oxide nanoparticles are highly stable molecular imaging agents in vitro, both before and after chemical linking of fluorochromes and biomolecules, but yet are labile and/or degradable in vivo.

In one aspect, the invention provides a fluorescent metal oxide nanoparticle comprising: (a) a core comprising metal oxide; (b) a polymer coating chemically linked to the core; and c) a plurality of fluorochromes chemically linked to the coating, wherein the nanoparticle has a molar extinction coefficient of at least 1,000,000 $M^{-1}cm^{-1}$, and emits fluorescent light upon illumination with light absorbable by the plurality of fluorochromes.

The fluorescent metal oxide nanoparticles have molar extinction coefficient from about 1,000,000 $M^{-1}cm^{-1}$ to about 30,000,000 $M^{-1}cm^{-1}$, from about 1,250,000 $M^{-1}cm^{-1}$ to about 20,000,000 $M^{-1}cm^{-1}$, from about 1,500,000 $M^{-1}cm^{-1}$ to about 10,000,000 $M^{-1}cm^{-1}$, or from about 1,750,000 $M^{-1}cm^{-1}$ to about 7,500,000 $M^{-1}cm^{-1}$. In a preferred embodiment, the fluorescent metal oxide nanoparticles have a molar extinction coefficient from about 2,000,000 $M^{-1}cm^{-1}$ to about 5,000,000 $M^{-1}cm^{-1}$. The nanoparticles comprises from about 4 to about 100 or from about 20 to about 60 fluorochromes chemically linked to the coating.

In another aspect, the invention provides a fluorescent metal oxide nanoparticle comprising: (a) a core comprising metal oxide; (b) a non-crosslinked polymer coating chemically linked to the core; and (c) from about 10 to about 300 fluorochromes chemically linked to the coating. In certain embodiments, the fluorescent metal oxide nanoparticles can comprise from about 15 to about 100 fluorochromes per particle, or from about 20 to about 60 fluorochromes per particle.

In another aspect, the invention provides a fluorescent metal oxide nanoparticle comprising: (a) a core comprising metal oxide; (b) a polymer coating chemically linked to the core; and (c) a plurality of fluorochromes chemically linked to the polymer, wherein the nanoparticle, when illuminated with light of a wavelength absorbable by the fluorochromes chemically linked to the core, retains at least 50% of the fluorescence obtained from substantially the same number of free fluorochromes (i.e., not attached to a nanoparticle) when measured under the same conditions.

In certain embodiments, the nanoparticle retains from about 50% to about 100% or from about 75% to about 95% of the fluorescence obtained from substantially the same number of free fluorochromes when measured under the same conditions. The nanoparticles can comprise from about 100 to about 300 fluorochromes per particle, or from about 15 to about 100 fluorochromes per particle, or from about 20 to about 60 fluorochromes per particle.

The present invention further provides fluorescent metal oxide nanoparticles that also have magnetic properties, for example, are paramagnetic or are superparamagnetic, that can be used as multi-modality imaging agents (for example, during optical imaging and magnetic resonance imaging).

The fluorescent metal oxide nanoparticles can be formulated into a pharmaceutical composition suitable for administration to a subject, for example, an animal and/or a human subject. The pharmaceutical composition can include the fluorescent metal oxide nanoparticles and one or more stabilizers in a physiologically relevant carrier.

In addition, the present invention provides methods for in vitro and in vivo imaging using the fluorescent metal oxide nanoparticles. With respect to in vivo imaging, the method comprises (a) administering to a subject fluorescent metal oxide nanoparticles of the invention; (b) allowing the nanoparticles to distribute within the subject; (c) exposing the subject to light of a wavelength absorbable by the fluorochromes of the nanoparticle and/or to magnetic radiation; and (d) detecting an optical and/or magnetic signal emitted by the nanoparticle. The signal emitted by the particles (optical and/or magnetic signal) can be used to construct an image, either alone or as fused (combined or composite) images. In one embodiment, one or more of the images are a tomographic image, however, it is understood that the tomographic images can be co-registered or fused with an image obtained by other imaging modalities including tomographic and non-tomographic modalities. Furthermore, it is understood that the foregoing steps can be repeated at predetermined intervals thereby permitting evaluation of the subject over time.

The subject may be a vertebrate, for example, a mammal, for example, a human. The subject may also be a non-vertebrate (for example, C. elegans, drosophila, or another model research organism, etc.) used in laboratory research.

Information provided by such in vivo imaging approaches, for example, the presence, absence, or level of emitted signal can be used to detect and/or monitor a disease in the subject. Exemplary diseases include, without limitation, autoimmune disease, bone disease, cancer, cardiovascular disease, environmental disease, dermatological disease, immunologic disease, inherited disease, infectious disease, metabolic disease, neurodegenerative disease, ophthalmic disease, and respiratory disease. In addition, in vivo imaging can be used to assess the effect of a compound or therapy on a specified molecular target by using the fluorescent metal oxide nanoparticles, wherein the subject is imaged prior to and after treatment with the compound or therapy, and the corresponding images are compared.

In addition, the fluorescent metal oxide nanoparticles can be used to label a biological sample, for example, cells, ex vivo. The sample, for example, cells, can be derived directly from a subject or from another source (for example, from another subject, cell culture, etc.). The fluorescent metal oxide nanoparticles can be mixed with the cells to effectively label the cells, and the resulting labeled cells injected into a subject. This method can be used for monitoring trafficking and localization of certain cell types, including T-cells, immune cells, tumor cells, and stem cells, and other cell types. In particular, this method may be used to monitor cell-based therapies.

With respect to in vitro imaging, the fluorescent metal oxide nanoparticles can be used in a variety of in vitro assays. For example, an exemplary in vitro imaging method comprises: (a) contacting a sample with the nanoparticles of the invention; (b) allowing the nanoparticles to (i) become activated by and/or (ii) bind to a biological target; (c) optionally removing unactivated or unbound nanoparticles; (d) illuminating the sample with light of a wavelength absorbable by the fluorochromes of the nanoparticles; and (e) detecting signal emitted from the nanoparticles thereby to determine whether the nanoparticles have been activated or bound by the biological target.

The sample can be a liquid or solid sample containing, for example, primary cells, cell cultures, or tissue. The biological target can be, for example, a cell, an aggregation of cells, a tissue or tissue sample, a structure (both on the macrocellular level (for example, bone or tissue) or on a subcellular cellular level (for example, a mitochrondia or nucleus)), and a cellular component, for example, a protein (for example, an enzyme or structural protein), lipid, nucleic acid or polysaccharide.

The fluorescent metal oxide nanoparticles can be incorporated into a kit, for example, a kit with optional instructions for using the nanoparticles in in vivo or in vitro imaging methods. The kit optionally can include components that aid in the use of the fluorescent metal oxide nanoparticles for the disclosed methods, such as buffers, and other formulating agents. Alternatively, the kit can include medical devices that aid in the administration of fluorescent metal oxide nanoparticles to subjects.

The fluorescent metal oxide nanoparticles and methods provide various advantages and have broad applications in both research and clinical settings. For example, the fluorescent metal oxide nanoparticles and methods provide for the ability to acquire molecular images and optionally, high resolution anatomical images using one imaging agent. The new fluorescent metal oxide nanoparticles and methods can provide insight into specific molecular abnormalities that form the basis of many diseases and can be used to assess efficacy of established and novel targeted therapies at the molecular level. This, in turn, is expected to have an impact in drug development, drug testing, disease diagnosis, and choosing appropriate therapies and therapy changes in a given patient. Other features and advantages of the invention will be apparent from the following figures, detailed description, and the claims.

BRIEF DESCRIPTION OF THE DRAWINGS

FIG. 16 is a graph showing the "brightness" of two exemplary fluorescent metal oxide nanoparticles of the present invention (represented by ■ and ○) compared to fluorescent CLIO nanoparticles (represented by ♦ and x).

FIG. 17 is a picture showing the image of blood vessels in a mouse ear using the nanoparticles described in Example 2 at 24 hours using intravital microscopy.

DETAILED DESCRIPTION OF THE INVENTION

Figure 1:
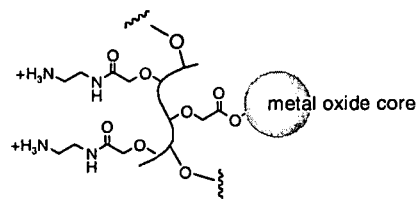
FIG. 1 is a schematic representation of an amino functionalized metal oxide nanoparticle (in a protonated form) comprising a carboxymethylated polyvinyl alcohol polymer coat with at least 2 amines per metal oxide core. The shaded sphere represents the metal oxide core.

The invention is based, in part, upon the discovery that it is possible to produce fluorescent metal oxide nanoparticles that are exceptionally fluorescent or, in other words, have very high fluorescent brightness upon excitation. The nanoparticles are stable and biocompatible, and can be used in a variety of in vivo and in vitro assays and imaging protocols.

I. Fluorescent Metal Oxide Nanoparticles

In one aspect, the invention provides a fluorescent metal oxide nanoparticle comprising: (a) a core comprising metal oxide; (b) a polymer coating chemically linked to the core; and c) a plurality of fluorochromes chemically linked to the coating, wherein the nanoparticle has a molar extinction coefficient of at least 1,000,000 $M^{-1}cm^{-1}$, and emits fluorescent light upon illumination with light absorbable by the plurality of fluorochromes.

As used herein, the term "chemically linked" is understood to mean connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions.

The fluorescent metal oxide nanoparticles have a molar extinction coefficient from about 1,000,000 $M^{-1}cm^{-1}$ to about 30,000,000 $M^{-1}cm^{-1}$, from about 1,250,000 $M^{-1}cm^{-1}$ to about 20,000,000 $M^{-1}cm^{-1}$, from about 1,500,000 $M^{-1}cm^{-1}$ to about 10,000,000 $M^{-1}cm^{-1}$, or from about 1,750,000 $M^{-1}cm^{-1}$ to about 7,500,000 $M^{-1}cm^{-1}$. In a preferred embodiment, the fluorescent metal oxide nanoparticles have a molar extinction coefficient from about 2,000,000 $M^{-1}cm^{-1}$ to about 5,000,000 $M^{-1}cm^{-1}$. The nanoparticles comprise from about 4 to about 100, from about 5 to about 90, from about 10 to about 80, from about 15 to about 70, or from about 20 to about 60 fluorochromes chemically linked to the coating. The polymer can be crosslinked or non-crosslinked, however, non-crosslinked polymers are preferred.

In another aspect, the invention provides a fluorescent metal oxide nanoparticle comprising: (a) a core comprising metal oxide; (b) a non-crosslinked polymer coating chemically linked to the core; and (c) from about 10 to a about 300 fluorochromes chemically linked to the coating. In certain embodiments, the fluorescent metal oxide nanoparticles comprise from about 15 to about 70 fluorochromes per particle, or from about 20 to about 60 fluorochromes per particle.

As used herein, the term "non-crosslinked polymer coating" is understood to mean a polymer in which few or no individual polymer chains have reacted with one another to produce intermolecular crosslinks. In the non-crosslinked polymer coating, less than 10% of the total polymer content of the coating comprises crosslinked multimers of different polymer chains.

As used herein, the term "crosslinked polymer coating" is understood to mean a polymer coating in which functional groups on a first polymer chain (including branches) have reacted with functional groups on second, different polymer chain (including branches) to form a polymer network. A cross linked polymer has a molecular weight significantly higher than the original starting polymer.

In another aspect, the invention provides a fluorescent metal oxide nanoparticle comprising: (a) a core comprising metal oxide; (b) a polymer coating associated with the core; and (c) a plurality of fluorochromes chemically linked to the polymer, wherein the nanoparticle, when illuminated with light of a wavelength absorbable by the fluorochromes chemically linked to the polymer coated core retains at least 50% of the fluorescence obtained from substantially the same number (for example, within 10% of the number) of free fluorochromes (i.e., not attached to a nanoparticle) when measured under the same conditions.

It is appreciated that the nanoparticles of the invention experience significantly less autoquenching than do other nanoparticles (for example, CLIO particles) in the art. In certain embodiments, the nanoparticles retain from about 50% to about 100% or from about 75% to about 95% of the fluorescence obtained from substantially the same number of free fluorochromes when measured under the same conditions. In addition, under certain circumstances (for example, in the presence of albumin or polyethylene glycol), it is appreciated that the nanoparticles may also exhibit a relative fluorescence greater than 100% when compared to the fluorescence derived from substantially the same number of free fluorochromes when measured under the same conditions. The nanoparticles can comprise from about 100 to about 300 fluorochromes per particle, or from about 15 to about 70 fluorochromes per particle, or from about 20 to about 60 fluorochromes per particle. The polymer can be crosslinked or non-crosslinked, however, non-crosslinked polymers are preferred.

(a) Metal Oxide Core Considerations

In certain embodiments, the metal oxide of the core can be monodisperse or polydisperse. The size of the metal oxide core can range from about 1 to 25 nm in diameter. In certain preferred embodiments the size of the metal oxide core is about 3 to 10 nm in diameter. It is appreciated that the nanoparticles generally are larger than the metal oxide core because of the polymer coating. For example, in certain embodiments, the resulting nanoparticles have a diameter ranging from about 10 nm to about 100 nm.

In certain embodiments, the metal oxide core comprises iron oxide including, but not limited to $Fe_3O_4$ or $Fe_2O_3$. Alternatively, the metal oxide can also comprise cobalt, magnesium, samarium, zinc, or mixtures of these and other metals with or without iron. The metal oxide core can be magnetic, paramagnetic and superparamagnetic. The term "magnetic" means materials of high positive magnetic susceptibility. In one preferred embodiment, a superparamagnetic form of iron oxide is used. Superparamagnetic iron oxide is one of the highly magnetic forms (magnetite, non-stoichiometric magnetite, gamma-ferric oxide) that have a magnetic moment of greater than about 30 EMU/gm Fe at 0.5 Tesla and about 300 K. When the magnetic moment is measured over a range of field strengths, it shows magnetic saturation at high fields and lacks magnetic remanence when the field is removed.

(b) Polymer Considerations

The polymer coating can comprise a natural or synthetic polymer, or a combination or a co-polymer thereof. The polymer coating is chemically linked to the metal oxide core to keep the metal oxides dispersed from each other. In one embodiment the polymer coating is not a continuous film around the magnetic metal oxide, but is a "mesh" or "cloud" of extended polymer chains that are chemically linked to the metal oxide core. In one embodiment one or more than one polymers can form two or more coatings or shells. The polymer may be linear, or moderately or highly branched. The polymer coating can be about 5 to 20 nm thick or more.

Exemplary polymers include polymethylmethacrylate, polyvinylalcohol (PVA), polyacrylic acid, polyglutamic acid, polylactic acid, polyhydroxylethyl acrylate, carboxylated polyethylene glycol, polyethylene maleic acid, and polylactic-co-glycolic acid.

Polycarboxyl polymers are particularly useful for the polymer coatings. A polycarboxyl polymer is a polymer with more than one carboxyl group per polymer, and the resulting polymer coating comprises a plurality of carboxyl moieties. In one embodiment, the polymer contains between 450 µmol and 5000 µmol COOH per gram of polymer as determined by titration. In another embodiment, the polymer contains between 600 µmol and 1500 µmol COOH per gram of polymer as determined by titration. When such polymers are used, the coating can be chemically linked to the core through a subset of the carboxyl moieties.

Carboxyl group bearing polyamino acids can be used and include, for example, polycarboxylated polymers, for example, polyaspartate or polyglutamate. In one embodiment, the polymer coating can be carboxylated dendrimers, which are highly branched polycarboxyl polymers. Carboxylated dendrimers are available commercially.

In certain preferred embodiments, the polymer coating comprises polycarboxylated polymers that have a molecular weight between about 5 and about 200 kDa, or between about 5 and about 50 kDa, or between about 5 and about 20 kDa. Synthetic and naturally occurring hydroxylated polymers can be used in the synthesis of polycarboxylated polymers and include polysaccharides like dextran, starch or cellulose and polyvinyl alcohol. Exemplary polycarboxylated polymers include, for example, carboxymethyl starch (CMS), carboxymethylated hydroxyethyl starch (CMHES), carboxymethyl guar (CMG), carboxymethylated hydroxypropyl starch (CMHPS), and carboxymethyl cellulose. In certain embodiments, the polymer coating is carboxymethylated polyvinyl alcohol.

In certain embodiments, the fluorescent metal oxide nanoparticles further comprise a plurality of other functional groups on the polymer including but not limited to hydroxyl groups, carboxyl groups and reactive primary amine groups that are not chemically linked with the metal oxide core. One or more fluorochromes, biomolecules and/or biological modifiers can be chemically linked to the polymer coating using these functional groups either directly or by using linker or spacer molecules as described below.

In certain embodiments, when carboxylated polymers are used in the synthesis of the nanoparticles, the resulting polymer coated nanoparticle has two classes of carboxyl groups with very different chemical reactivities. Some carboxyl groups are shielded from further chemical reaction by chemical linkage of the polymer and the surface of the metal oxide core. Some surface carboxyl groups that are not chemically linked with the metal oxide core can be converted to produce a different reactive group, for example, a primary amino group. As a result, the nanoparticle can comprise from about 100 to about 300 reactive amines per particle, from about 150 to about 250 reactive amines per particle. Some of these reactive primary amines can then be used to attach one or more fluorochrome molecules to the polymer coating with or without the use of a linker or spacer moiety. The remaining primary amines on the nanoparticle polymer coating can be used to attach biomolecules and/or biological molecules to form targeted imaging agents with or without the use of a linker or spacer moieties.

When the carbodiimide activated carboxylated nanoparticles of the invention are reacted with a large excess of diamine, one of the nitrogen atoms reacts with the carboxyl group to provide a peptide bond, while a second exists as a primary amine suitable for further chemistry. This produces amino-functionalized metal oxide nanoparticles (see, FIG. 1). Hence in certain embodiments, the fluorescent metal oxide nanoparticles of the invention can have a characteristic general structure that includes a peptidyl bond and a primary amino group on the polymer coating. The nature of the diamine provides a linker arm of varying lengths and chemistries for chemically linking biomolecules and/or compounds. Non-limiting examples of diamines include ethylenediamine (EDA), propylenediamine, spermidine, spermine, hexanediamine, and diamine amino acids, such as homolysine, lysine, ornithine, diaminobutyric acid and diaminopropionic acid. It is preferred that the reaction with diamine is performed under conditions that prevent cross-linking between nanoparticles. This is accomplished by using a large excess of diamine.

(c) Linking Chemistries

It is understood that the fluorochromes and/or the biomolecules and/or the biological modifiers can be chemically linked either directly or indirectly (for example, via a linker or spacer) to the polymer coat of the nanoparticle. Useful linker moieties include both natural and non-natural amino acids and nucleic acids, peptides, as well as synthetic linker molecules such as aminoethyl maleimide. When the linker is a peptide, the peptide optionally may include proteolytic cleavage site that can be cleaved with a variety of agents, for example, an enzyme.

There is no particular size or content limitation of the linker or spacer. The carboxyl functionalized iron oxide based nanoparticles can be reacted with amines containing other functional groups such as maleimide, dithiopyridyl, thiol, azide, alkene, or alkyne. Alternatively, the carboxyl functionalized iron oxide based nanoparticles can be reacted with amines containing solubilizing groups such as sulfonates or phosphates. Alternatively, the azide functionalized iron oxide based nanoparticles can be reacted with substituted alkynes in an azide-acetylene Huisgen [3+2] cyclo addition. In another embodiment the linker can be a fluorochrome with two or more functional groups.

The linkers can be homofunctional linkers or heterofunctional linkers. The amino-functionalized metal oxide based nanoparticles can be reacted with bifunctional cross-linkers designed to react with amino groups. Particularly useful conjugation reagents are N-hydroxysuccinimide (NHS) esters, which react with the amine group of the nanoparticle, and have a second moiety (such as maleimide) that can react with the sulfhydryl group of another molecule. Other particularly useful linker moieties are bifunctional crosslinkers such as N-succinimidyl 3-(2-pyridyldithio)propionate (SPDP) that give the nanoparticles illustrated in FIG. 2, long chain-SPDP, maleimidobenzoic acid-N-hydroxysuccinimide ester (MBS), succinimidyl trans-4-(maleimidylmethyl) cyclohexane-1-carboxylate (SMCC), succinimidyl iodoacetate (SIA) that give nanoparticles illustrated in FIG. 3, and others that are known in the art and are commercially available.

Figure 4:
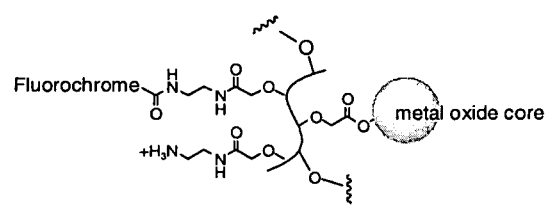
FIG. 4 is a schematic representation of the amino functionalized metal oxide nanoparticle described in FIG. 1 chemically linked to a fluorochrome via a carbonyl moiety. There can be 1 or more fluorochromes and up to 500 amines (z=0 to 500) per metal oxide core. The shaded sphere represents the metal oxide core.
Figure 5:
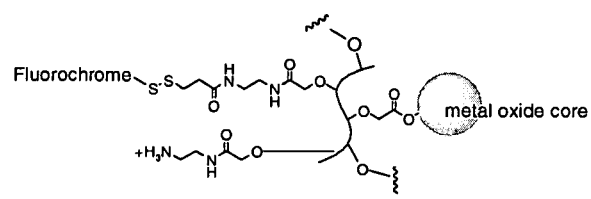
FIG. 5 is a schematic representation of an exemplary nanoparticle resulting from a reaction between a thiol-containing-fluorochrome and the 3-(2-pyridyldithio)-propionyl derivatized amino functionalized metal oxide nanoparticle shown in FIG. 2. There can be one or more fluorochromes and up to 500 amines (z=0 to 500) per metal oxide core. The shaded sphere represents the metal oxide core.

In certain embodiments, the fluorochromes are chemically linked to the polymer coating of the nanoparticles using reactive NHS esters groups on the fluorochrome which react with the amine group of the amino-functionalized metal oxide nanoparticle as illustrated in FIG. 4. In certain other embodiments, carboxylic acid groups on the fluorochromes can be activated in situ by activating agents known in the art, such as 2-(1H-benzotriazole-1-yl)-1,1,3,3,-tetramethyluronium hexafluorophosphate (HBTU), 1-ethyl-3-(3'-dimethyl-aminopropyl)carbodiimide hydrochloride (EDC), N,N'-dicyclohexylcarbodiimide (DCC), N,N'-disuccinimidyl carbonate (DSC). In other embodiments, fluorochromes containing a sulfhydryl or thiol group, can be chemically linked to the metal oxide nanoparticles via a bifunctional cross-linker that has a second moiety that can react with a sulfhydryl (thiol) group. Such crosslinking agents include, for example and as described above, SPDP, long chain-SPDP, SIA, MBS, SMCC, and others that are well known in the art. This process provides certain preferred fluorescent metal oxide nanoparticles (one example of which is shown in FIG. 5).

In one embodiment, when the polymer is carboxymethylated-PVA, the carboxymethyl-PVA can be linked to the fluorochrome through a diamine moiety represented by: $NH_2$—$(CH_2)_n$—$NH_2$, wherein n is an integer from 1 to 12.

(d) Fluorochrome Considerations

As discussed herein, a plurality of fluorochromes can be linked to the polymer. A "fluorochrome" includes but is not limited to, a fluorochrome, a fluorophore, a fluorochrome quencher molecule, any fluorescent organic or inorganic dye, metal chelate that changes the fluorescence of any entity, or any fluorescent enzyme substrate, including protease activatable enzyme substrates.

In certain preferred embodiments, the fluorochromes are red and near infrared fluorochromes (NIRFs) with absorption and emission maximum between about 400 and about 1200 nm, more preferably between about 600 nm and about 900 nm. It will be appreciated that the use of fluorescent metal oxide nanoparticles with excitation and emission wavelengths in other spectrums can also be employed in the compositions and methods of the present invention.

The NIRFs preferably have an extinction coefficient of at least 50,000 $M^{-1}cm^{-1}$ per fluorochrome molecule in aqueous medium. The NIRFs preferably also have (1) high quantum yield (i.e., quantum yield greater than 5% in aqueous medium), (2) narrow excitation/emission spectrum, spectrally separated absorption and excitation spectra (i.e., excitation and emission maxima separated by at least 15 nm), (3) high chemical and photostability, (4) nontoxicity, (5) good biocompatibility, biodegradability and excretability, and (6) commercial viability and scalable production for large quantities (i.e., gram and kilogram quantities) required for in vivo and human use.

In particular, certain carbocyanine or polymethine fluorescent dyes can be used to produce the fluorescent metal oxide nanoparticles of the invention, for example, those described in U.S. Pat. No. 6,747,159; U.S. Pat. No. 6,448,008; U.S. Pat. No. 6,136,612; U.S. Pat. Nos. 4,981,977; 5,268,486; U.S. Pat. No. 5,569,587; U.S. Pat. No. 5,569,766; U.S. Pat. No. 5,486,616; U.S. Pat. No. 5,627,027; U.S. Pat. No. 5,808,044; U.S. Pat. No. 5,877,310; U.S. Pat. No. 6,002,003; U.S. Pat. No. 6,004,536; U.S. Pat. No. 6,008,373; U.S. Pat. No. 6,043,025; U.S. Pat. No. 6,127,134; U.S. Pat. No. 6,130,094; U.S. Pat. No. 6,133,445; also WO 97/40104, WO 99/51702, WO 01/21624, and EP 1 065 250 A1; and Tetrahedron Letters 41, 9185-88 (2000).

Various near infrared fluorochromes are commercially available and can be used to construct probes according to this invention. Exemplary fluorochromes include the following: Cy5.5, Cy5 and Cy7 (GE Healthcare); AlexaFlour660, AlexaFlour680, and AlexaFluor750 (Invitrogen); VivoTag680, VivoTag-S680, and VivoTag-S750 (VisEn Medical); Dy677, Dy682, Dy752 and Dy780 (Dyomics); DyLight547, and DyLight647 (Pierce). Table 1 lists a number of exemplary fluorochromes useful in the practice of the invention together with their spectral properties.

TABLE 1

| Fluorochrome | $\epsilon_{max}$ $M^{-1}cm^{-1}$ | Absorbance max (nm) |
|---|---|---|
| Cy5 | 250,000 | 649 |
| Cy5.5 | 250,000 | 675 |
| Cy7 | 250,000 | 743 |
| AlexaFlour660 | 132,000 | 663 |
| AlexaFlour680 | 184,000 | 679 |
| AlexaFlour750 | 280,000 | 749 |
| VivoTag680 (VT680) | 100,000 | 670 |
| VivoTag-S680 | 220,000 | 674 |
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |

In one embodiment, the fluorochrome comprises molecule of Formula A:

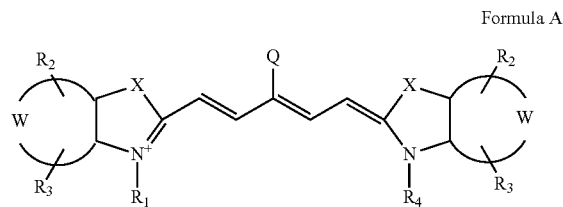

Formula A and its salts, wherein:

X is $C(CH_3)_2$

W represents non-metal atoms required to form a benzo-condensed, a naphtho-condensed or a pyrido-condensed ring, $R_1$ is selected from the group consisting of $(CH_2)_nCH_3$, $(CH_2)_nSO_3^-$ and $(CH_2)_nSO_3H$, wherein n is an integer selected from 0 to 6 when $R_1$ is $(CH_2)_nCH_3$, and n is an integer selected from 2 to 6 when $R_1$ is $(CH_2)_nSO_3^-$ or $(CH_2)_nSO_3H$, $R_4$ is selected from the group consisting of $(CH_2)_nCH_3$, $(CH_2)_nSO_3^-$ and $(CH_2)_nSO_3H$, wherein n is an integer selected from 0 to 6 when $R_4$ is $(CH_2)_nCH_3$, and n is an integer selected from 2 to 6 when $R_4$ is $(CH_2)_nSO_3^-$ or $(CH_2)_nSO_3H$, $R_2$ and $R_3$ are independently selected from the group consisting of H, a sulphonic acid moiety and a sulphonate moiety, Q is selected from a group consisting of (i) a carboxyl functionalized heterocyclic ring, (ii) a carboxyl functionalized nitrogen containing heterocyclic ring, (iii) a carboxyl functionalized nitrogen containing 6-membered heterocyclic ring, such as pyridine, pyrimidone, pyrazine, and pyridazine, (iv) a carboxyl functionalized nitrogen containing 6-membered heterocyclic ring, such as pyridine, (v) a carbonyl functionalized nitrogen containing 6-membered heterocyclic ring, such as pyridine, (vi) an isonicotinic acid, nicotinic acid and picolinic acid, and a group selected from:

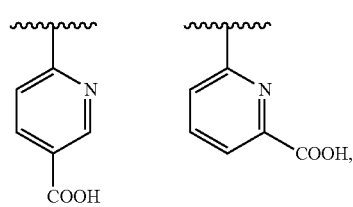

wherein, the carboxyl group is also in the form of an ester, an activated ester or carbonyl halide that is capable of reacting with nucleophiles, and can be, for example, a CO-Obenzotriazolyl, CO—ON-hydroxysuccinimidyl, CO-Otetrafluorophenyl, CO-Opentafluorophenyl, CO-Oimidazole, and CO-Op-nitrophenyl.

In one embodiment, the fluorochrome is:

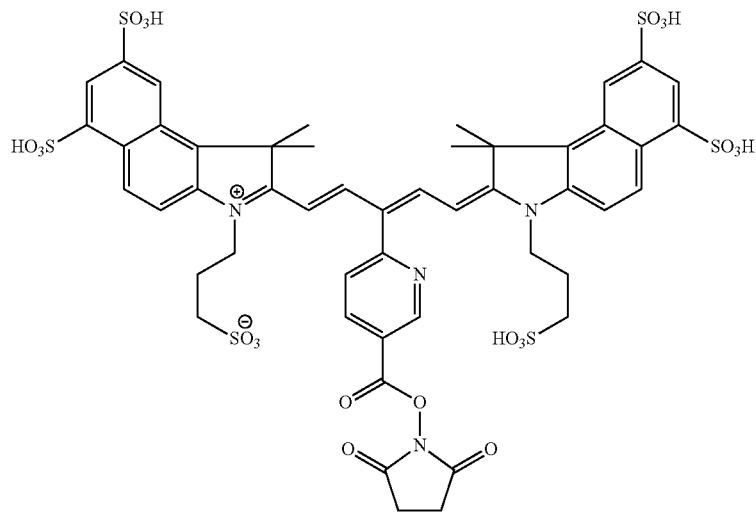

In another embodiment, the fluorochrome is:

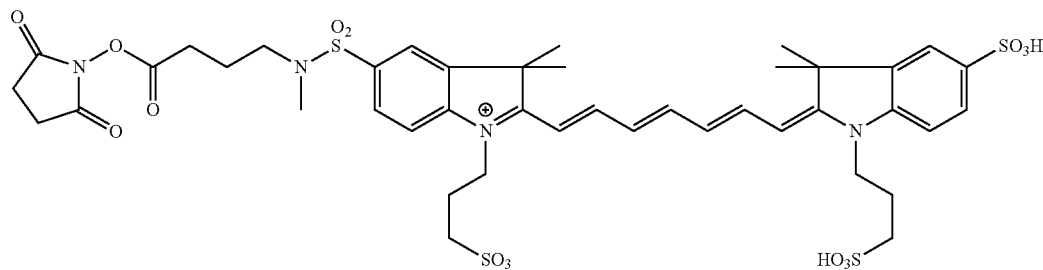

In another embodiment, the fluorochrome is:

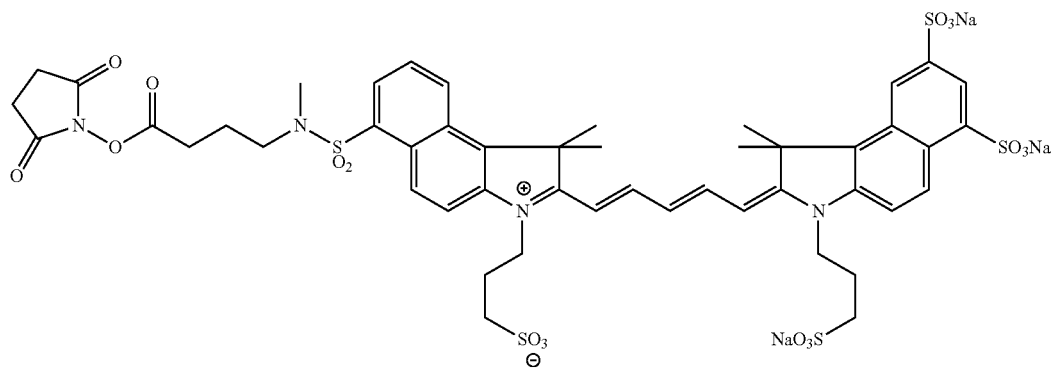

One or more fluorochrome molecules can be chemically linked to the amino-functionalized metal oxide nanoparticle to produce the fluorescent metal oxide nanoparticles of the present invention.

In certain embodiments, the fluorescent metal oxide nanoparticles comprise from about 10 to about 300 fluorochromes per particle, from about 15 to about 100 fluorochromes per particle, or from about 20 to about 60 fluorochromes per particle. The fluorescent nanoparticle contains a number of conjugated fluorochromes to achieve a composite epsilon in the range from about 1,000,000 to about 30,000,000 $M^{-1}cm^{-1}$, from about 1,250,000 $M^{-1}cm^{-1}$ to about 20,000,000 $M^{-1}cm^{-1}$, from about 1,500,000 $M^{-1}cm^{-1}$ to about 10,000,000 $M^{-1}cm^{-1}$, from about 1,750,000 $M^{-1}cm^{-1}$ to about 7,500,000 $M^{-1}cm^{-1}$. In a preferred embodiment, the nanoparticle has a molar extinction coefficient from about 2,000,000 $M^{-1}cm^{-1}$ to about 5,000,000 $M^{-1}cm^{-1}$.

The extinction coefficient of the particles can be calculated as the ratio of the absorbance of dye at its absorption maxima (for example at ~670 nm for VivoTag 680) in a 1 cm path length cell to the concentration of particles, ($\epsilon=A/cl$, where A is absorbance, c is molar concentration and l is path length in cm). Nanoparticle concentration can be determined by dividing the metal oxide concentration (in the case of the iron oxide nanoparticles, the iron concentration) by the approximate number of metal atoms in each particle (for example, in case of the iron oxide nanoparticles, 8000 iron atoms may be used the calculation). The metal atom content can be measured using a variety of techniques known in the art. For example, when the iron content of an iron oxide nanoparticle is to be determined, the following approach can be used. 10 µL of an iron particle solution is digested in 6 M HCl at 50-60° C. for one hour. Then, 25 µL of the digested iron solution is added to 975 µL of phenanthroline reagent solution (120 mL methanol, 1 g 1,10-phenanthroline, 2.3 g sodium acetate, 0.7 mL glacial acetic acid and 1.0 g sodium ascorbate. The ferroin complex thus formed ($Fe^{II}$(phenanthroline)$_3$) then is quantified by its absorption at 510 nm and then the concentration determined by methods known to those skilled in the art, for example, by interpolation of the results on a calibration curve.

In addition, the nanoparticles of the invention exhibit limited autoquenching relative to other particles, for example, CLIO particles, known in the art. For example, when illuminated with light of a wavelength absorbable by the plurality of fluorochromes chemically linked to the core, the nanoparticle retains at least 50%, for example, from about 50% to about 100%, or from about 75% to about 95% of the fluorescence obtained from substantially the same number of free fluorochromes (i.e., fluorochromes not attached to a particle) when measured under the same conditions.

It is contemplated that autoquenching occurs due to interactions between individual fluorochromes in close proximity to one another and typically results in substantially reduced fluorescence output. Autoquenching sets a limit on usable fluorochrome loading levels for a nanoparticle, and by extension, limits maximum fluorescence payload a single nanoparticle can deliver. Thus, for a given nanoparticle platform, simply conjugating more fluorochromes to the particle is in itself not sufficient to create a nanoparticle with higher overall fluorescence.

The fluorescent metal oxide nanoparticles of the invention are significantly brighter than other fluorescent metal oxide nanoparticles known in the art. The "brightness" of the fluorescent nanoparticles of the invention is achieved through (i) an increase in the total number of reactive sites available for conjugation of fluorochromes, which is a function of the composition and structure of the polymer coating of the particle and (ii) a lower degree of autoquenching of the conjugated fluorochromes, which is a function of the property of the fluorochrome itself and the local environment on the polymer coating. The resulting nanoparticles of the invention provide a significant improvement in the "brightness" of the fluorescent nanoparticles, not achieved by those already known in the prior art. These features are shown in Example 14.

(e) Additional Particle Modifications

In certain embodiments, the fluorescent metal oxide nanoparticle further comprise one or more (for example, from about 1 to about 100) biomolecules chemically linked to the polymer coating. A "biomolecule" is a moiety that can be chemically linked to the fluorescent metal oxide nanoparticles of the present invention and changes or enhances accumulation, uptake, biodistribution, biocompatibility, elimination, targeting, binding, and/or recognition of the fluorescent metal oxide nanoparticle.

Biomolecules include, but are not limited to, proteins, peptides, antibodies and antigen binding fragments thereof (for example, Fab, Fab', (Fab')$_2$ fragments), single chain antibodies or sFvs, oligonucleotides, aptamers, glycoproteins, ligands for cell receptors, polysaccharides, cell receptors, enzyme substrates, enzyme cofactors, biotin, hormones, neurohormones, neurotransmitters, growth factors, cytokines, lymphokines, lectins, selectins, toxins, nucleic acids, oligonucleotides and derivatives thereof. Other targeting and delivery approaches using various biomolecules can also be used, such as folate-mediated targeting (Leamon & Low, *Drug Discovery Today*, 6:44-51, 2001), transferrin, vitamins, carbohydrates and ligands that target internalizing receptors, including, but not limited to, asialoglycoprotein receptor, somatostatin, nerve growth factor, oxytocin, bombesin, calcitonin, arginine vasopressin, angiotensin II, atrial natriuretic peptide, insulin, glucagons, prolactin, gonadotropin, various opioids and urokinase-type plasminogen activator.

Non-limiting examples include small molecules and peptide sequences to target integrins such as $\alpha_v\beta_3$ and $GP\alpha_{IIb}\beta_3$, bombesin, CD4 and VCAM-1. Also included are peptides for Hepsin, SPARC, PAR1, colon cancer, Factor 13. Exemplary peptides include: (Hepsin) Ile-Pro-Leu-Val-Leu-Pro-Leu (SEQ ID NO.: 1); (SPARC) Ser-Pro-Pro-Thr-Gly-Ile-Asn (SEQ ID NO.: 2); (VCAM1) Val-His-Pro-Lys-Gln-His-Arg (SEQ ID NO.: 3); (Cathepsin K) Val-His-Pro-Lys-Gln-His-Arg (SEQ ID NO.: 4); (E-selection binding peptide) Cys-Asp-Ser-Asp-Ser-Asp-Ile-Thr-Trp-Asp-Gln-Leu-Trp-Asp-Asp-Leu-Met-Lys (SEQ ID NO.: 5); and (Tat) Arg-Arg-Arg-Arg-Gly-Arg-Arg-Arg-Arg (SEQ ID NO.: 6). Also included are membrane, transmembrane, and nuclear translocation signal compounds and sequences, which can be derived from a number of sources including, without limitation, viruses and bacteria. Non-limiting examples include HIV-tat derived peptides, protamine, and polyArg and Arg-rich peptides. Importantly, biomolecules can also include synthetic compounds including but not limited to small molecule drugs, phototherapeutic molecules and derivatives thereof. Also included are antibiotics such as vancomycin, clindamycin, chemotherapeutics such as doxorubicin, molecules such as glycine, derivatives of AMG706, Zactima™, MP-412, erlotinib, sorafenib, dasatinib, lestaurtinib, lapatinib, XL647, XL999, MLN518, PKC412, ST1571, AMN107, AEE788, OSI-930, OSI-817, sunitinib, AG-013736; molecules that target/inhibit VEGF receptors, PDGF receptor, HER2, SSKI, EphB4, EGFR, FGFR, VEGFR-2, VEGFR-3, serine/threonine and receptor kinases, FLT-3, type III RTKs, c-KIT, Bcr-Abl, CSF-1R, CCR-2, RET and VDGF-2.

In some embodiments, attaching one or more biomolecules to the nanoparticle does not alter the activity of the biomolecules. One or more biomolecules, including different biomolecules, can be chemically linked to the fluorescent metal oxide nanoparticles. In certain preferred embodiments, biomolecules are chemically linked in a polyvalent or multivalent fashion. Some preferred embodiments have more than one biomolecule chemically linked to a fluorescent metal oxide nanoparticle, where the biomolecules are all the same or different. In other preferred embodiments, the biomolecules themselves are bivalent, or multivalent, i.e., have two or more target binding site or substrate per molecule. This includes but is not limited to multivalent small molecule and peptide sequences.

Figure 6:
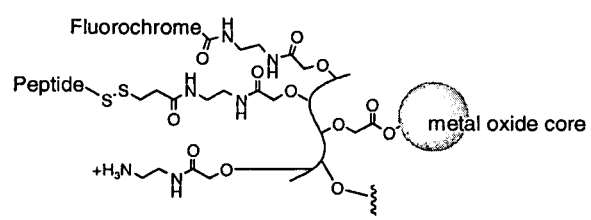
FIG. 6 is a schematic representation of an exemplary nanoparticle, where the nanoparticle of FIG. 4 is functionalized with a thiol-containing-peptide utilizing the 3-(2-pyridyldithio)-propionyl linker. There can be one or more 1 fluorochromes, one or more 1 peptides, and up to 500 amines (z=0 to 500) per metal oxide core. The shaded sphere represents the metal oxide core.

In one embodiment, the fluorescent metal oxide nanoparticles further comprise one or more biomolecules wherein the biomolecule is a peptide (see, FIG. 6). The peptide can be 1-200 amino acids in length, 2-100 amino acids in length, 3-75 amino acids in length, 4-35 amino acids in length and 5-15 amino acids in length.

The number of peptides chemically linked to the fluorescent metal oxide nanoparticles can be in the range of 1-200 peptides per particle, 2-100 peptides per particle, or 3-50 peptides per particle.

In one embodiment, the fluorescent metal oxide nanoparticle further comprises one or more biomolecules wherein the biomolecule is a peptide with the sequence Arg-Arg-Arg-Arg-Gly-Arg-Arg-Arg-Arg-Gly-Cys-amide (SEQ ID NO: 7). In another embodiment, the fluorescent metal oxide nanoparticle further comprises of a one or more biomolecules wherein the biomolecule is a peptide having the sequence D-Arg-D-Arg-D-Arg-D-Arg-D-Arg-D-Arg-D-Arg-Cys-amide (SEQ ID NO: 8) or Arg-Arg-Arg-Arg-Arg-Arg-Arg-Cys-amide (SEQ ID NO: 9). In another embodiment, the fluorescent metal oxide nanoparticle further comprises one or more biomolecules wherein the biomolecule is cyclo(Arg-Gly-Asp-D-Phe-Cys) (SEQ ID NO: 10) or Arg-Gly-Asp-Ser (SEQ ID NO: 11) or cyclo(Arg-Gly-Asp-D-Phe-Lys) (SEQ ID NO: 12).

In another embodiment, fluorochromes or other reporting groups can be chemically linked to the particles via a peptide linker. The peptides optionally comprise a protease cleavage site that permits the fluorochrome or the other reporting group to be removed via cleavage of the peptide. This can result in enhanced fluorescence for a fluorochrome. Other reporting groups include but are not limited to radioisotopes or luminescent molecules. In one embodiment, the fluorescent metal oxide nanoparticle further comprises one or more biomolecules wherein the biomolecule is Gly-Pro-Leu-Gly-Val-Arg-Gly-Gly-Cys-amide (SEQ ID NO: 13), and a fluorochrome is chemically linked to the Gly N-terminus. In one embodiment, the fluorescent metal oxide nanoparticle further comprises one or more biomolecules wherein the biomolecule is Val-His-Pro-Lys-Gln-His-Arg-Gly-Gly-Ser-Lys(FITC)-Gly-Cys-amide (SEQ ID NO: 14).

In one embodiment, the fluorescent metal oxide nanoparticle further comprises one or more biomolecules where the biomolecule is chloroisatoic anhydride or isatoic anhydride. In one embodiment, the fluorescent metal oxide nanoparticle further comprises of one or more biomolecules where the biomolecule is a photosensitizer or phototherapy reagent. Exemplary photosensitizers include, without limitation, Chlorin e6, Photofrin, Lutrin, Antrin, aminolevulinic acid, hypericin, porphyrins, and porphyrin derivatives, for example, benzoporphyrin derivative.

In one embodiment, the fluorescent metal oxide nanoparticle further comprises one or more biomolecules where the biomolecule is a radiolabel. Radioisotopic form of metals such as copper, gallium, indium, technetium, yttrium, and lutetium can be chemically linked to the resulting nanoparticles and can be used for nuclear imaging or therapeutic applications. Exemplary radiolabels include, without limitation, 99m-Tc, 111-In, 64-Cu, 67-Ga, 186-Re, 188-Re, 153-Sm, 177-Lu, and 67-Cu.

In one embodiment, the fluorescent metal oxide nanoparticle further comprises a chelating agent. Chelators, for example, polyamine-polycarboxylate chelators or iminoacetic acid chelators can be chemically linked to the fluorescent metal oxide nanoparticles.

Chelators or bonding moieties for diagnostic radiopharmaceuticals are selected to form stable complexes with the radioisotopes that have imageable gamma ray or positron emissions, such as 99m-Tc, 111-In, 64-Cu, 67-Ga. Chelators are selected from diaminedithiols, monoamine-monoamidedithiols, triamide-monothiols, monoamine-diamide-monothiols, diaminedioximes, and hydrazines. The chelators generally are tetradentate with donor atoms selected from nitrogen, oxygen and sulfur, cyclic and acyclic polyaminocarboxylates such as diethylenetriaminepentaacetic acid (DTPA), 1,4,7,10-tetraazacyclododecane-1,4,7,10-tetraacetic acid (DOTA), (DO3A), 2-benzyl-DOTA, alpha-(2-phenethyl) 1,4,7,10-tetraazazcyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

Chelators or bonding moieties for therapeutic radiopharmaceuticals are selected to form stable complexes with the radioisotopes that have alpha particle, beta particle, Auger or Coster-Kronig electron emissions, such as 186-Re, 188-Re, 153-Sm, 177-Lu, 67-Cu. Chelators can be selected from diaminedithiols, monoamine-monoamidedithiols, triamide-monothiols, monoamine-diamide-monothiols, diaminedioximes, and hydrazines, cyclic and acyclic polyaminocarboxylates such as DTPA, DOTA, DO3A, 2-benzyl-DOTA, alpha-(2-phenethyl) 1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

Chelators for magnetic resonance imaging contrast agents can be selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl) 1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

In other certain embodiments, one or more biological modifiers can be chemically linked to the fluorescent metal oxide nanoparticle. The biological modifiers can be used to alter the biological and/or fluorescent properties of the nanoparticle. For example, the biological modifiers render the nanoparticles more useful for biological imaging, that is, for example, more water soluble, or more dispersible in media for administration, with increased binding specificity, or less immunogenic, or less toxic, or with reduced nonspecific binding, altered biodistribution and pharmacokinetic compared to the single (or native) polymer coated nanoparticles. For example, a coating of methoxypolyethylene glycol (mPEG) or polypeptides may function to modify the pharmacodynamics and blood clearance rates of the fluorescent metal oxide based nanoparticles in vivo. Other biological modifiers may be chosen to accelerate the clearance of the nanoparticles from background tissue, such as muscle or liver, and/or from the blood, thereby reducing the background interference and improving image quality. Additionally, the biological modifier may also be used to favor a particular route of excretion, e.g., via the kidneys rather than via the liver, or to prevent or promote opsonization or accumulation in the reticuloendothelial system. The biological modifiers may also aid in formulating probes in pharmaceutical compositions or may be used to alter or preserve the optical properties of the nanoparticles. In particular, chemical linking of polyethylene glycol (PEG) or a derivative thereof to nanoparticles and/or biomolecules can result in longer blood residence time (longer circulation) and decreasing immunogenicity. Optionally, fluorochromes and/or biomolecules can be chemically linked (using appropriate functional groups) to the biological modifier. Exemplary biological modifiers include PEG and derivatives thereof, phospholipids, amino acids and peptides, phospholipid PEG, carbohydrates, such as dextran, sulfonates and polysulfonates.

In certain embodiments, the fluorescent metal oxide nanoparticles are coupled to a PEG moiety. The PEG moiety may be conjugated to reactive amines on the nanoparticle via a carboxyl functionality. Alternatively, the PEG modifier can be conjugated to the fluorescent metal oxide nanoparticles by using a thiol reactive cross linker and then reacting with a thiol group on the PEG.

Figure 7:
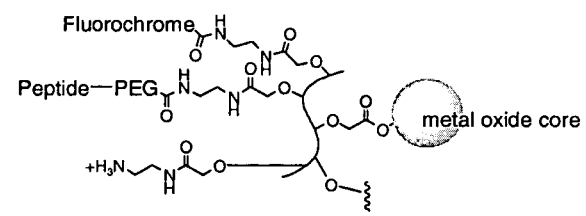
FIG. 7 is a schematic representation of an exemplary nanoparticle where the nanoparticle of FIG. 4 is functionalized with a polyethyleneglycol (PEG) moiety to which a peptide is chemically linked. There can be one or more fluorochromes, one or more peptides, one or more PEG, and up to 500 amines (z=0 to 500) per metal oxide core. The shaded sphere represents the metal oxide core.

The omega position of PEG contains a hydroxyl group or a methoxy group. In another embodiment, the PEG contains an amino group in the omega position. This amino group on the PEG can in turn be coupled to a variety of molecules independently selected from, for example, fluorochromes, and biomolecules (see, FIG. 7). The PEG can have a molecular weight between 100 Da and 20,000 Da. In certain embodiments, the PEG is methoxyPEG$_{(5000)}$-succinimidylpropionate (mPEG-SPA), methoxyPEG$_{(5000)}$-succinimidylsuccinate (mPEG-SS). Such PEGS are commercially available from Nektar Therapeutics or SunBiowest.

In general, the chemical linking of biomolecules and/or biological modifiers does not adversely affect the fluorescent properties of the fluorescent metal oxide nanoparticles (i.e., it does not quench the fluorescence, or shift the fluorescence outside the preferred excitation or emission spectra). Additionally, chemical linking of biomolecules and/or biological modifier may help preserve the fluorescent and/or magnetic properties of the fluorescent metal oxide nanoparticles.

In other embodiments, the fluorescence of the fluorescent metal oxide nanoparticles is enhanced by the addition of biomolecules and/or biological modifier. In one aspect of the invention the fluorescence enhancement occurs due to a change in the overall charge or charge distribution of the resulting fluorescent metal oxide nanoparticles.

In other embodiments, the fluorescence of the fluorescent metal oxide nanoparticles is diminished by chemical linking of biomolecules and/or biological modifiers. The fluorescence can be recovered ("activation") partly or fully due to a 1) a conformational change of the biomolecules and/or biological modifier; 2) partial or complete cleavage of the biomolecules and/or biological modifiers, including linkers or spacers used to chemically link biomolecules and/or fluorochromes to the nanoparticle or 3) cleavage of a certain section of the biomolecules and/or biological modifiers.

The "activation" of a fluorescent metal oxide nanoparticle imaging probe is understood to mean a change to the probe that alters a detectable property, e.g., an optical and/or magnetic property, of the probe. This includes, but is not limited to, a modification, alteration, or binding (covalent or non-covalent) of the probe that results in a detectable difference in properties, e.g., optical and/or magnetic properties of the probe, e.g., changes in the fluorescence and/or magnetic signal amplitude (e.g., dequenching and quenching), change in wavelength, fluorescence lifetime, spectral properties, or polarity. Optical properties include wavelengths, for example, in the visible, ultraviolet, NIR, and infrared regions of the electromagnetic spectrum. Activation can be, without limitation, by enzymatic cleavage, enzymatic conversion, phosphorylation or dephosphorylation, conformation change due to binding, enzyme-mediated splicing, enzyme-mediated transfer, hybridization of complementary DNA or RNA, analyte binding, such as association with an analyte such as $Na^+$, $K^+$, $Ca^{2+}$, $Cl^-$, or another analyte, change in hydrophobicity of the environment and chemical modification.

In one embodiment, a biomolecule that diminishes the fluorescence signal of the fluorescent metal oxide nanoparticles is a peptide that contains several Arg residues or is polyArg or is protamine. In certain embodiments, the polyArg is between 3 to 30 Arg residues. In another embodiment, the molecular weight (MW) of the polyArg is about 4,000 Da.

In one embodiment of the invention, the fluorescent metal oxide nanoparticle further comprises of one or more fluorescently labeled peptides wherein the fluorescence of the nanoparticle is enhanced upon activation. In a preferred embodiment of the invention, the enhancement of fluorescence occurs due to the cleavage of the peptide sequence by a protease.

In other embodiments, a quencher molecule is used to quench the fluorescent signal of the fluorescent metal oxide nanoparticle. The quencher molecule is chemically linked such that it quenches the optical properties of the fluorescent metal oxide nanoparticle. The quencher can be chemically linked, for example, to a portion of the fluorescent metal oxide nanoparticle (for example, to the nanoparticle polymer coating, the additional polymer coating, or to the biomolecule). Upon activation of the fluorescent metal oxide nanoparticle, the fluorescent metal oxide nanoparticle is dequenched. By adopting these activated and unactivated states of a fluorescent metal oxide nanoparticle in a living animal or human, the fluorescent metal oxide nanoparticle will exhibit different signal intensities, depending on whether fluorescent metal oxide nanoparticle has been activated or is in its active state. It is therefore possible to determine whether the fluorescent metal oxide nanoparticle is in its active state or inactive state in a living organism by identifying a change in the signal properties of the fluorescent metal oxide nanoparticle. In addition, because the fluorescent metal oxide nanoparticle can be designed such that the quencher molecule quenches the fluorescence of the fluorescent metal oxide nanoparticle when it is not activated, the fluorescent metal oxide nanoparticle can be designed such that the fluorescent metal oxide nanoparticle exhibits little or no signal until it is activated.

There are a number of quenchers available and known to those skilled in the art including, but not limited to 4-{[4-(dimethylamino)-phenyl]-azo}-benzoic acid (DABCYL), QSY®-7 (9-[2-[(4-carboxy-1-piperidinyl)sulfonyl]phenyl]-3,6-bis(methylphenylamino)-xanthylium chloride) (Molecular Probes, Inc., OR), QSY®-33 (Molecular Probes, Inc., OR), and fluorescence dyes such as Cy5 and Cy5.5 (e.g., 2-[5-[3-[6-[(2,5-dioxo-1-pyrrolidinyl)oxy]-6-oxohexyl]-1,3-dihydro-1,1-dimethyl-6,8-disulfo-2H-benz[e]indol-2-ylidene]-1,3-pentadienyl]-3-ethyl-1,1-dimethyl-6,8-disulfo-1H-benz[e]indolium, inner salt) (Schobel, Bioconjugate 10:1107, 1999). Other quenching strategies can be used, for example, using various solvents to quench fluorescence of the fluorescent metal nanoparticles.

In other embodiments of the invention, the fluorescent metal oxide nanoparticles can be chemically linked to a dicarboxylic acid including but not limited to succinic acid, glutaric acid, suberic acid, or adipic acid. In certain aspects of the invention, chemically linking of dicarboxylic acids to the fluorescent metal oxide nanoparticles enhances the fluorescence of the nanoparticle. In certain embodiments, it enhances the fluorescence of the nanoparticle by at least 50%.

Figure 2:
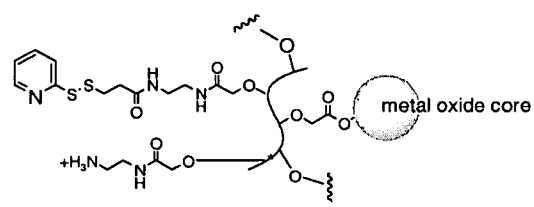
FIG. 2 is a schematic representation of the amino functionalized metal oxide nanoparticle shown in FIG. 1 chemically linked to a 3-(2-pyridyldithio)-propionyl moiety. There can be one or more 3-(2-pyridyldithio)-propionyl moieties and up to 500 amines (z=0 to 500) per metal oxide core. The shaded sphere represents the metal oxide core.
Figure 3:
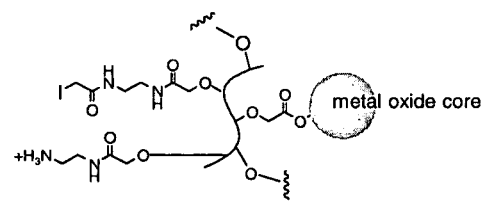
FIG. 3 is a schematic representation of the amino functionalized metal oxide nanoparticle described in FIG. 1 chemically linked to an iodoacetyl moiety. There can be one or more iodoacetyl moieties and up to 500 amines (z=0 to 500) per metal oxide core. The shaded sphere represents the metal oxide core.
Figure 8:
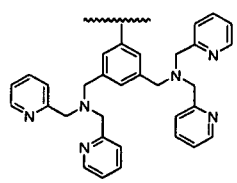
FIG. 8 is a schematic representation of two N,N-dipicolylamine moieties linked to a meta-dimethylphenyl group.
Figures 9A, 9B:
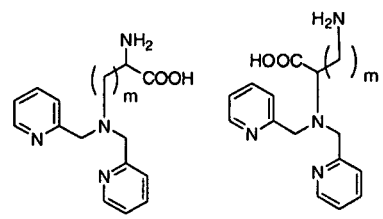
FIGS. 9A and 9B are schematic representations of an N,N-dipicolylamine moiety on an amino acid containing two amines.
Figure 10:
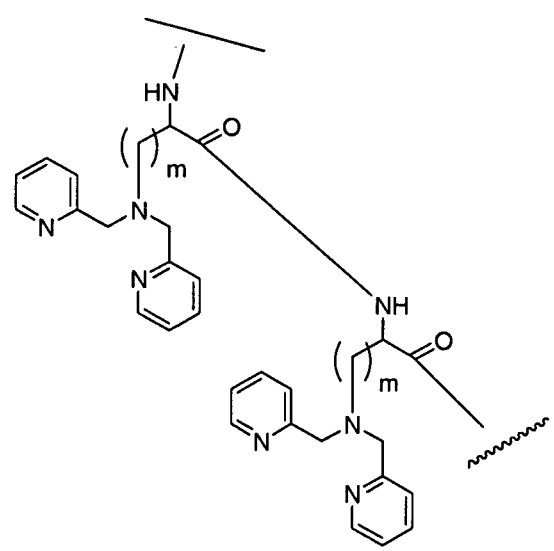
FIG. 10 is a schematic representation of a peptide fragment containing two N,N-dipicolyl moieties.
Figure 11:
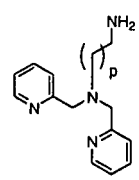
FIG. 11 is a schematic representation of an N,N-dipicolyl moiety linked to a diaminoalkanes.
Figure 12:
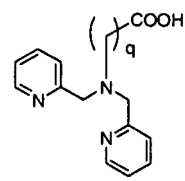
FIG. 12 is a schematic representation of an N,N-dipicolyl moiety on an amino acid.
Figure 13:
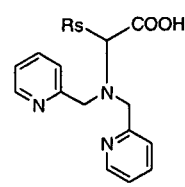
FIG. 13 is a schematic representation of an N,N-dipicolyl moiety on an alpha-amino acid.

In one embodiment, the fluorescent metal oxide nanoparticle is conjugated to an N,N-dipicolylamine moiety. The N,N-dipicolylamine moiety can reside on a phenyl or phenylene group such as is shown in FIG. 8. The N,N-dipicolylamine moiety can also reside on either amine of lysine (m=4), homolysine (m=5), ornithine (m=3), diaminobutyric acid (m=2), and diaminopropionic acid (m=1), as illustrated in FIG. 9A and FIG. 9B, or p-aminomethylphenylalanine, which in turn can be chemically linked directly or indirectly to the fluorescent metal oxide nanoparticles via the amino or carboxyl groups. Alternatively, the N,N-dipicolylamine moiety can reside on either amine of lysine (m=4), homolysine (m=5), ornithine (m=3), diaminobutyric acid (m=2), and diaminopropionic acid (m=1), which in turn forms a part of a peptide chain (see, FIG. 10) that can be chemically linked to the fluorescent metal oxide nanoparticle. Alternatively, the N,N-dipicolyamine moiety can reside on either amine of ethylenediamine (p=1), propylenediamine (p=2), and other diaminoalkanes (p=3-12), as illustrated in FIG. 11, and 1,2-diaminocyclohexane, which in turn can be chemically linked directly or indirectly to the fluorescent metal oxide nanoparticle via the second amine. In a further embodiment of the invention the N,N-dipicolyamine moiety can reside on the amine of an amino acid (q=1-12, (see, FIG. 12); Rs=$C_1$-$C_{10}$ containing moiety, (see, FIG. 13), linear or cyclic, optionally substituted with N, O, S containing moieties), which in turn can be chemically linked to directly or indirectly to the fluorescent metal oxide nanoparticles via the carboxyl functionality.

Figure 14:
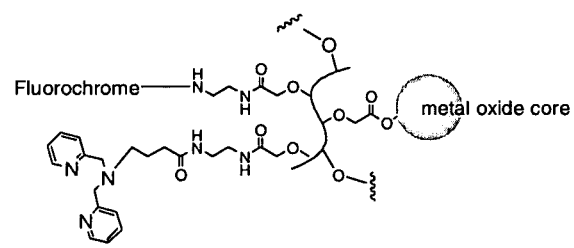
FIG. 14 is a schematic representation of an exemplary nanoparticle, wherein the nanoparticle show in FIG. 4 is functionalized with an N,N-dipicolyl moiety. There can be one or more 1 fluorochromes, one or more 1 N,N-dipicolyl moieties and up to 500 amines per metal oxide core. The shaded sphere represents the metal oxide core.
Figure 15:
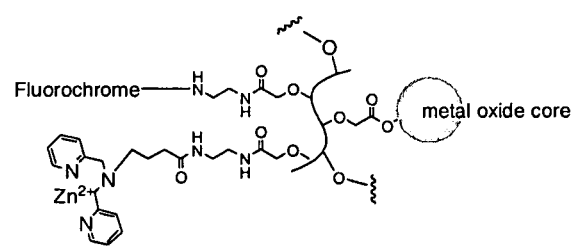
FIG. 15 is a schematic representation of an exemplary nanoparticle wherein the nanoparticle shown in FIG. 14 is complexed to $Zn^{2+}$. The shaded sphere represents the metal oxide core.

In one embodiment, the fluorescent metal oxide nanoparticle further comprises two or more N,N-dipicolylamine moieties as illustrated in FIG. 14. In another embodiment, the fluorescent metal oxide nanoparticle further comprises two or more N,N-dipicolylamine moieties which can coordinate cations such as $Zn^{2+}$ as illustrated in FIG. 15. In one embodiment, the fluorescent metal oxide nanoparticle further comprises two or more N,N-dipicolylamine moieties that can be used for imaging cell death, injury or apoptosis in vitro or in vivo.

In certain embodiments, the fluorescent metal oxide nanoparticles can be degraded to yield their metal salts and polymer coating. In some preferred embodiments, the degradation yields iron salts and the polymer coating. In vivo, this results in the utilization of iron oxide, by incorporation of iron into red blood cells, and by the excretion and/or degradation of the polymer.

The fluorescent metal oxide nanoparticles can be water soluble or water dispersible (i.e., sufficiently soluble or suspendable in aqueous or physiological media solutions). The in vivo half-life of the fluorescent metal oxide nanoparticle can be designed to be at least about 10 minutes, but more preferably 30 minutes to many hours. The in vivo half-life of the fluorescent metal oxide nanoparticle preferably is a time (for example, at least about one hour) sufficient to perform luminal delineating studies, such as gastrointestinal imaging or major vessel angiography, fluorescence (micro) angiography, perfusion and angiogenesis studies. In a preferred embodiment, the fluorescent metal oxide nanoparticle imaging probe is water soluble or dispersible in aqueous media, and is biocompatible i.e., non-toxic having, for example, an $LD_{50}$ of greater than about 50 mg/kg body weight. The imaging probes also preferably do no have any phototoxic properties and/or display little or no serum protein binding affinity.

For in vivo use, the compositions of the present invention can be provided in a formulation suitable for administration to a subject, for example, an animal or a human. Accordingly, the formulations include the fluorescent metal oxide nanoparticles together with a physiologically relevant carrier suitable for the desired form and/or dose of administration. The term, "physiologically relevant carrier" is understood to mean a carrier in which the fluorescent metal oxide nanoparticles are dispersed, dissolved, suspended, admixed and physiologically tolerable, i.e., can be administered to, in, or on the subject's body without undue discomfort, or irritation, or toxicity. The preferred carrier is a fluid, preferably a liquid, more preferably an aqueous solution; however, carriers for solid formulations, topical formulations, inhaled formulations, ophthalmic formulations, and transdermal formulations are also contemplated as within the scope of the invention.

It is contemplated that the nanoparticles can be administered orally or parenterally. For parenteral administration, the nanoparticles can be administered intravenously, intramuscularly, cutaneously, percutaneously, subcutaneously, rectally, nasally, vaginally, and ocularly. Thus, the composition may be in the form of, e.g., solid tablets, capsules, pills, powders including lyophilized powders, colloidal suspensions, microspheres, liposomes granulates, suspensions, emulsions, solutions, gels, including hydrogels, pastes, ointments, creams, plasters, irrigation solutions, drenches, osmotic delivery devices, suppositories, enemas, injectables, implants, sprays, or aerosols. The pharmaceutical compositions can be formulated according to conventional pharmaceutical practice (see, e.g., Remington: The Science and Practice of Pharmacy, 20th edition, 2000, ed. A. R. Germaro, Lippincott Williams & Wilkins, Philadelphia, and Encyclopedia of Pharmaceutical Technology, eds. J. Swarbrick and J. C. Boylan, 1988-1999, Marcel Dekker, New York).

II. Characterization of the Nanoparticles by In Vitro Testing

After a fluorescent metal oxide nanoparticle has been designed, synthesized, and optionally formulated, it can be tested in vitro by one skilled in the art to assess its biological and performance characteristics. For instance, different types of cells grown in culture can be used to assess the biological and performance characteristics of the fluorescent metal oxide nanoparticle. Cellular uptake, binding or cellular localization of the fluorescent metal oxide nanoparticle can be assessed using techniques known in the art, including, for example, fluorescent microscopy. By way of example, the fluorescent metal oxide nanoparticles can be contacted with a sample for a period of time and then optionally washed to remove any free fluorescent metal oxide nanoparticles. The sample can then be viewed using a fluorescent microscope equipped with appropriate filters matched to the optical properties of the fluorescent metal oxide nanoparticle. Fluorescence microscopy of cells in culture is also a convenient means for determining whether uptake and binding occurs in one or more subcellular compartments. Tissues, tissue sections and other types of samples such as cytospin samples can also be used in a similar manner to assess the biological and performance characteristics of the fluorescent metal oxide nanoparticle. Other fluorescent detection methods including, but not limited to flow cytometry, immunoassays, hybridization assays, and microarray analysis can also be used.

III. Applications of the Nanoparticles

The fluorescent metal oxide nanoparticles can be used in a variety of in vivo and in vitro applications. These applications are discussed in the following sections.

(a) In Vivo Applications

The invention provides novel fluorescent metal oxide nanoparticles which can be used in a variety of imaging, for example, optical imaging applications. For a review of optical imaging techniques, see, e.g., Alfano et al., *Ann. NY Acad. Sci.* 820:248-270, 1997.

An imaging system useful in the practice of this invention typically includes three basic components: (1) an appropriate light source for causing fluorescent metal oxide nanoparticle excitation, (2) a system for separating or distinguishing emissions from light used for fluorochrome excitation, and (3) a detection system. This detection system can be hand-held or incorporated into other useful imaging devices such as intraoperative microscopes and/or viewers.

Preferably, the light source provides monochromatic (or substantially monochromatic) light. The light source can be a suitably filtered white light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., *Proc. Natl. Acad. Sci. USA* 91:4887-4891, 1994; Ntziachristos et al., *Proc. Natl. Acad. Sci. USA* 97:2767-2772, 2000; and Alexander, *J. Clin. Laser Med. Surg.* 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., *J. Photochem. Photobiol. B* 52:131-135, 1999), ovarian cancer (Major et al., *Gynecol. Oncol.* 66:122-132, 1997), colon and rectum (Mycek et al., *Gastrointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et al., *Urol. Int.* 63:27-31, 1999; and Riedl et al., *J. Endourol.* 13:755-759, 1999), lung (Hirsch et al., *Clin Cancer Res* 7:5-220, 2001), brain (Ward, *J. Laser Appl.* 10:224-228, 1998), esophagus, and head and neck regions can be employed in the practice of the present invention.

Other types of light gathering components are catheter-based devices, including fiber optics devices. Such devices are particularly suitable for intravascular imaging. See, e.g., Teamey et al., *Science* 276:2037-2039, 1997; and *Circulation* 94:3013, 1996.

Still other imaging technologies, including phased array technology (Boas et al., *Proc. Natl. Acad. Sci. USA* 91:4887-4891, 1994; Chance, *Ann. NY Acad. Sci.* 838:29-45, 1998), optical tomography (Cheng et al., *Optics Express* 3:118-123, 1998; and Siegel et al., *Optics Express* 4:287-298, 1999), intravital microscopy (Dellian et al., *Br. J. Cancer* 82:1513-1518, 2000; Monsky et al, *Cancer Res.* 59:4129-4135, 1999; and Fukumura et al., *Cell* 94:715-725, 1998), confocal imaging (Korlach et al., *Proc. Natl. Acad. Sci. USA* 96:8461-8466, 1999; Rajadhyaksha et al., *J. Invest. Dermatol.* 104:946-952, 1995; and Gonzalez et al., *J. Med.* 30:337-356, 1999) and fluorescence molecular tomography (FMT) (Nziachristos et al., *Nature Medicine* 8:757-760, 2002; U.S. Pat. No. 6,615,063, PCT Application No. WO 03/102558, and PCT US/03/07579) can be used with the nanoparticles of the invention. Similarly, the nanoparticles can be used in the IVIS® Imaging System (Xenogen, Alameda, Calif.), the SoftScan® or the eXplore Optix™ (Advanced Research Technologies, Montreal, Canada) system.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

Optical imaging and measurement techniques include, but are not limited to, fluorescence imaging, luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography.

For fluorescent metal oxide nanoparticles that have magnetic properties, MRI imaging well known in the art can also be applied in the practice of the invention. For a review of MRI techniques see Westbrook, Handbook of MRI Technique, $2^{nd}$ Edition, 1999, Blackwell Science. It is possible that images obtained, for example, by fluorescent molecular tomography and by magnetic resonance imaging can be co-registered or fused with one another to provide additional information about the item being imaged. Furthermore, multi-modality imaging systems (i.e., combined optical and MR imaging systems) can be used to create combined optical MR images.

In addition, the compositions and methods of the present invention can be used in combination with other imaging compositions and methods. For example, the nanoparticles of the present invention can be imaged by optical imaging protocols either alone or in combination with other traditional imaging modalities, such as, X-ray, computed tomography (CT), MR imaging, ultrasound, positron emission tomography (PET), and single photon computerized tomography (SPECT). For instance, the compositions and methods of the present invention can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents or alternatively, the fluorescent metal oxide nanoparticles of the present invention may also contain imaging agents, such as iodine, gadolinium atoms and radioactive isotopes, which can be detected using CT, PET, SPECT, and MR imaging modalities in combination with optical imaging. The imaging agents can be linked to or incorporated in the nanoparticles.

The present invention further provides methods of in vivo imaging comprising (a) administering to a subject nanoparticles of the invention; (b) allowing the nanoparticles to distribute in the subject; (c) exposing the subject to (i) light of a wavelength absorbable by the fluorochromes chemically linked to the fluorescent metal oxide nanoparticles and/or (ii) magnetic radiation, and (d) detecting an optical and/or magnetic signal emitted by the fluorescent metal oxide nanoparticle. The foregoing steps, including, for example, steps (a)-(d), can be repeated at predetermined time intervals thereby to permit evaluation of the emitted signals of the nanoparticles in the subject over time. The illuminating and detecting steps (steps (c) and (d), respectively) can be performed using a planar imaging system, endoscope, catheter, tomographic system, hand-held optical imaging system, goggles, or an intraoperative microscope.

Before or during these steps, a detection system can be positioned around or in the vicinity of a subject (for example, an animal or a human) to detect optical and/or magnetic signals emitted from the subject. The emitted optical and/or MR signals can be processed to construct an image, for example, a tomographic or planar image. In addition, the processed signals can be displayed as images either alone or as fused (combined) images.

In addition, it is possible to practice an in vivo imaging method that selectively detects and images one or more molecular imaging probes simultaneously. In such an approach, for example, in step (a) noted above, two or more imaging probes whose signal properties are distinguishable from one another are administered to the subject, either at the same time or sequentially, wherein at least one of the molecular imaging probes is a fluorescent metal oxide nanoparticle. The use of multiple probes permits the recording of multiple biological processes, functions or targets.

The invention also features an in vivo imaging method where labeled cells are administered to the recipient. The cells can be labeled with the fluorescent metal oxide nanoparticles ex vivo. The cells can be derived directly from a subject or from another source (e.g., from another subject, cell culture, etc.). The fluorescent metal oxide nanoparticles can be mixed with the cells to effectively label the cells and the resulting labeled cells administered to the subject into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the fluorescent metal oxide nanoparticles, the choice of mode of administration, the dosages of nanoparticles administered to the subject, and the timing between administration of the nanoparticles and the exposure of the particles to light and/or magnetic radiation is within the level of skill in the art.

The methods of the invention can be used to determine a number of indicia, including tracking the localization of the fluorescent metal oxide nanoparticle in the subject over time or assessing changes or alterations in the metabolism and/or excretion of the fluorescent metal oxide nanoparticle in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions of the invention can be used to help a physician or surgeon to identify and characterize areas of disease, such as arthritis, cancers and specifically colon polyps, or vulnerable or unstable plaque, to distinguish diseased and normal tissue, such as detecting tumor margins that are difficult to detect using an ordinary operating microscope, e.g., in brain surgery, to help dictate a therapeutic or surgical intervention, e.g., by determining whether a lesion is cancerous and should be removed or non-cancerous and left alone, or in surgically staging a disease, e.g., intraoperative lymph node staging, sentinel lymph node mapping, or assessing intraoperative bleeding or to delineate tumor margins.

The methods and compositions of the invention can also be used in the detection, characterization and/or determination of the localization of a disease, especially early disease, the severity of a disease or a disease-associated condition, the staging of a disease, and/or monitoring a disease. The presence, absence, or level of an emitted signal can be indicative of a disease state. The methods and compositions of the invention can also be used to monitor and/or guide various therapeutic interventions, such as surgical procedures, and monitoring drug therapy, including cell based therapies. The methods of the invention can also be used in prognosis of a disease or disease condition. With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, skin, brain, gastrointestinal, mouth, esophageal, bone), cardiovascular disease (for example, atherosclerosis and inflammatory conditions of blood vessels, ischemia, stroke, thrombosis), dermatologic disease (for example, Kaposi's Sarcoma, psoriasis), ophthalmic disease (for example, macular degeneration, diabetic retinopathy), infectious disease (for example, bacterial, viral, fungal and parasitic infections, including Acquired Immunodeficiency Syndrome), immunologic disease (for example, an autoimmune disorder, lymphoma, multiple sclerosis, rheumatoid arthritis, diabetes mellitus), central nervous system disease (for example, a neurodegenerative disease, such as Parkinson's disease or Alzheimer's disease), inherited diseases, metabolic diseases, environmental diseases (for example, lead, mercury and radioactive poisoning, skin cancer), bone-related disease (for example, osteoporosis, primary and metastatic bone tumors, osteoarthritis) and a neurodegenerative disease.

The methods and compositions of the invention, therefore, can be used, for example, to determine the presence and/or localization of tumor cells, the presence and/or localization of inflammation, including the presence of activated macrophages, for instance in atherosclerosis or arthritis, the presence and in localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of the invention can also be used in identification and evaluation of cell death, injury, apoptosis, necrosis, hypoxia and angiogenesis. The methods and compositions can also be used for drug delivery and to monitor drug delivery, especially when drugs or drug-like molecules are chemically attached to the fluorescent metal oxide probes. Exemplary drug molecules include chemotherapeutic and cytostatic agents and photodynamic reagents including but not limited to Chlorin e6, Photofrin, Lutrin, Antrin, aminolevulinic acid, hypericin, porphyrins, and porphyrin derivatives, for example, benzoporphyrin derivative.

(b) In Vitro Applications

In addition, it is appreciated that the fluorescent metal oxide nanoparticles can be used in a variety of in vitro assays, for example, binding experiments, and in vitro imaging experiments. It is understood that the imaging technologies discussed in the previous section are also applicable to in vitro imaging experiments.

An exemplary in vitro imaging method comprises: (a) contacting a sample with the nanoparticles of the invention; (b) allowing the nanoparticles to (i) become activated by and/or (ii) bind to a biological target; (c) optionally removing unactivated or unbound nanoparticles; (d) illuminating the sample with light of a wavelength absorbable by the fluorochromes of the nanoparticles; and (e) detecting signal emitted from the nanoparticles thereby to determine whether the nanoparticles have been activated or bound by the biological target.

The sample can be a liquid or solid sample containing, for example, primary cells, cell cultures, or tissue. The biological target can be, for example, a cell, an aggregation of cells, a tissue or tissue sample, a structure (both on the macrocellular level (for example, bone or tissue) or on a subcellular cellular level (for example, a mitochrondia or nucleus)), and a cellular component, for example, a protein (for example, an enzyme or structural protein), lipid, nucleic acid or polysaccharide.

The fluorescent metal oxide nanoparticles can be used in a variety of in vitro ligand binding assays such as magnetic detection based assays (see, U.S. Pat. Nos. 6,046,585 and 6,275,031, U.S. Pat. No. 5,445,970; U.S. Pat. No. 4,219,335, Chemla, et. al. (2000) Proc Natl Acad. Sci. USA 97, 14268-72.). They can also be used in magnetic resonance based ligand binding assays such as those described in U.S. Pat. No. 5,164,297 and Perez et al. Nature Biotechnol. 2002, 20(8):816-20. The fluorescent magnetic nanoparticles can also be used for cell sorting and counting applications.

The fluorescent metal oxide nanoparticles can also be used for gene sequence recognition, labeled nucleic acid recognition molecules, including DNA, RNA, modified nucleic acid, PNA, molecular beacons, or other nucleic acid binding molecules (for example, small interfering RNA or siRNA), using techniques such as hybridization, ligation, cleavage, recombination, synthesis, sequencing, mutation detection, real-time polymerase chain reactions, in situ hybridization, and the use of microarrays. For example, for detecting a single stranded nucleic acid (i.e., mRNA, cDNA or denatured double-stranded DNA) in a sample, via nucleic acid hybridization principles, a fluorescent metal oxide nanoparticle chemically linked to a single-stranded nucleic acid is contacted with a sample containing one or more single stranded nucleic acids and the fluorescence of the fluorescent metal oxide nanoparticle imaging probe is detected, wherein the presence or level of fluorescence and/or magnetic signal emitted by the fluorescent metal oxide nanoparticle indicates the presence or amount of nucleic acid in the sample.

The invention will now be illustrated by means of the following examples, which are given for the purpose of illustration only and without any intention to limit the scope of the present invention.

EXAMPLES

The following non limiting examples demonstrate the synthesis of exemplary fluorescent nanoparticle. Representative materials and methods that may be used in preparing the materials of the invention are described further below. All chemicals and solvents (reagent grade) are used as commercially obtained without further purification. Particles are sized using a Zetasizer Nano S from Malvern. Particles are sized in 20 mM HEPES, pH 7 with 150 mM NaCl. Particle sizes are reported as the mean particle size based on volume distribution.

T1 and T2 relaxation times of aqueous solutions are determined using a Bruker NMS-120 Minispec MR spectrometer (Bruker Instruments, Canada) operating at a 0.47 T (20 MHz). Relaxivities R1 and R2 of the particles are calculated as the slopes of the curves of 1/T1 and 1/T2 vs. iron concentration. Characterization by FTIR is performed using a Perkin-Elmer Spectrum One IR spectrophotometer equipped with a diamond coated Zn/Se ATR crystal. About 1-2 µL of a solution of the particles is spotted on the ATR crystal and allowed to dry before obtaining spectra.

The presence of primary amino groups on the magnetic nanoparticles are ascertained by reaction with amine specific reagents such as TNBS or ninhydrin or SPDP with the intact nanoparticle. Since the carboxyl groups are protected by the metal oxide, they can be most easily analyzed after digestion of the metal oxide core and isolation of the polymeric coating. Digestion of metal oxide core is accomplished by treatment with acid and chelator. A pH below 5, or between 2 and 5, is sufficient. Chelators like citrate or EDTA enhance the solubility of iron and are added an amount sufficient to bind all metal ions. After digestion, the metal is removed by passage over a cation exchange column or metal removing chelating column such as Chelex. The polymer then is analyzed by IR and shows characteristic peaks from carboxyl groups. Polymers with carboxyl groups have characteristic absorption frequencies from the carbonyl group (C=O) of the carboxyl (1780 to 1710 $cm^{-1}$, strong) and the hydroxyl group (3000 to 2500 $cm^{-1}$, broad, variable).

Example 1—Synthesis of an Exemplary Fluorescent Metal Oxide Nanoparticle

Polyvinyl alcohol (6 kDa, Polysciences, 30 g) was dissolved in 140 mL of water by heating to 90° C. The solution was cooled and transferred to a 500 mL jacketed beaker equilibrated to 15° C. 100 mL of 50% NaOH was added slowly with vigorous stirring using an overhead stirrer until a smooth, relatively homogeneous suspension formed. Bromoacetic acid (100 g) was dissolved in 50 mL of water and added slowly with vigorous stirring, making sure the temperature stayed below 35° C. After complete addition, the mixture was stirred for 15 hours at room temperature, and then neutralized with 6 M HCl to pH~7. Carboxymethyl-polyvinylalcohol was precipitated by addition of cold ethanol, filtered, washed with 70% ethanol, pure ethanol, and ether and then dried under vacuum. The carboxyl content (in μmol/g) of the polymer was determined by titration to neutrality of an acidified sample of the polymer. A range of 450-850 μmol/g was found, depending on the amount of bromoacetic acid used.

The resulting carboxymethyl-polyvinylalcohol (37 g) was dissolved in 750 mL of hot, thoroughly degassed water, filtered through a 0.7μ glass fiber filter (Whatman) and cooled under nitrogen. Ferric chloride (1.86 mL of a 67% w/v solution, 7.6 mmol) was added slowly with stirring. The solution was transferred to a jacketed beaker with an overhead stirrer and cooled to 4° C. Ferrous chloride tetrahydrate (1.02 g, 5.2 mmol) was dissolved in degassed water and added slowly to the cold reaction mixture with constant stirring. Ammonium hydroxide (15 mL of 33%, 295 mmol) was added via syringe drop by drop with vigorous stirring over 10 minutes, during which the solution turned from orange to black. The temperature then was raised to 80° C. over 20 minutes and held at that temperature for 60 minutes. The solution was cooled, diluted with 400 mL deionized water and filtered successively through paper (3μ, Whatman), glass fiber (0.7μ, Whatman) and polyethersulfone (0.2μ, Millipore) filters. The filtered solution then was exhaustively dialyzed using a 300 kDa mwc hollow fiber cartridge and concentrated using a pressure filtration device to yield stable stock solutions of carboxylate functionalized iron oxide nanoparticles.

To about 200 mL of the stock solution (~400 mg Fe), ethylene diamine hydrochloride (70 mL of a 2 M solution adjusted to pH 6.5 with sodium hydroxide) and N-(3-dimethyl-aminopropyl)-N'-ethyl carbodiimide (EDC) (4 g) were combined in a 500 mL flask and allowed to react overnight at room temperature. The solution was dialyzed exhaustively using a 300 kDa mwc hollow fiber cartridge and concentrated with a pressure filtration device to yield stable solutions of amine functionalized iron oxide nanoparticles.

The resulting amine functionalized iron oxide nanoparticles (4.8 mL, 88 mM Fe) were combined with 1.0 mL of 0.1 M HEPES, pH 7.0 and 250 μL of 3.75 mM VivoTag™680 NHS ester (VisEn Medical, Woburn, Mass.) in DMSO and allowed to react at room temperature for 4 hours and then separated from unreacted dye to yield the nanoparticle of Formula I.

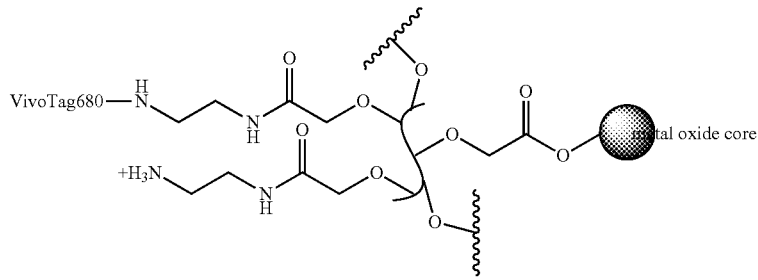

Example 2—Synthesis of an Exemplary Fluorescent Metal Oxide Nanoparticle with Polyethyleneglycol The nanoparticle of Formula I from Example 1 (500 μL, 6.8 mg/mL iron) and 50 μL 0.1 M HEPES, pH 7, was combined with 8 mg of mPEG-SPA (5 kDa) and allowed to react at room temperature overnight. The pegylated particles were purified by gel filtration using Biorad Biogel P-60 eluting with 1×PBS to yield a nanoparticle of Formula II.

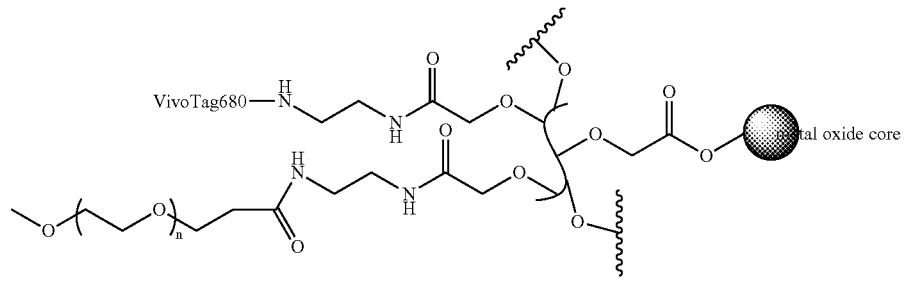

Example 3—Synthesis of Exemplary Succinylated Fluorescent Metal Oxide Nanoparticles Nanoparticles of Formula I from Example 1 (600 μL, 2.5 mg/mL iron) and 50 μL 0.1 M HEPES, pH 7, was combined with succinic anhydride (5 mg, 50 μmol) and reacted at room temperature for 5 hours. The succinylated particles were purified by gel filtration using Biorad Biogel P-60 eluting with 1×PBS to yield nanoparticles of Formula III.

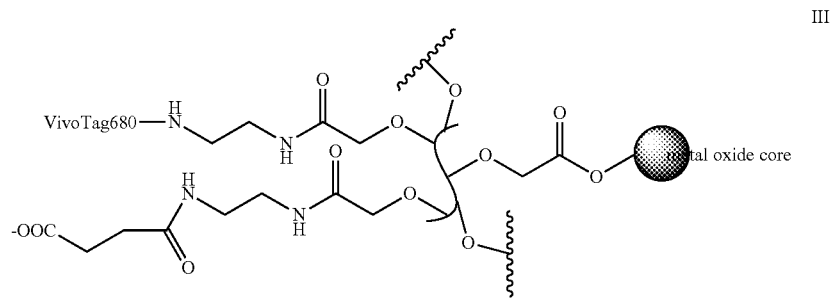

III

Example 4—Synthesis of Exemplary Fluorescent Metal Oxide Nanoparticle with Protamine Rhodamine labeled protamine (1.25 μmol, Josephson et al. *Bioconjugate Chem.*, 16(5): 1240-1245, 2005) was dissolved in 400 μL of DMSO and activated with EDC (40 mg, 0.21 mmol) and N-hydroxysuccinimide (18 mg, 0.16 mmol) for 4 hours at room temperature. The activated protamine solution then was added to 1.5 mL of the nanoparticles of Formula I (2 mg/mL iron) and 100 μL of 0.1 M HEPES, pH 7. The solution was allowed to react at room temperature overnight and purified by gel filtration using Biorad Biogel P-60 eluting with 1×PBS to yield nanoparticles of Formula IV.

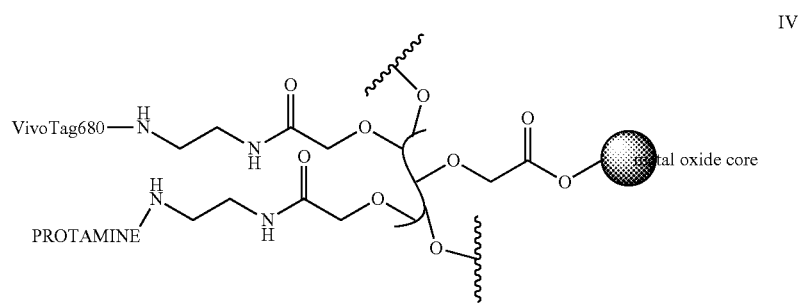

IV

Example 5-Synthesis of Exemplary Fluorescent Metal Oxide Nanoparticle with Peptide Biomolecule Nanoparticles of Formula I from Example 1 (600 μL of 2.5 mg/mL iron) were combined with 50 μL of 0.1 M HEPES, pH 7 and 4 mg of succinimidyl pyridinedithiopropionate (SPDP) in 100 μL DMSO and rotated for 5 hours at room temperature. The particles were separated from unreacted SPDP by gel filtration, eluting with 0.1 M HEPES, pH 7.0. N-Acetyl-Arg-Arg-Arg-Arg-Gly-Arg-Arg-Arg-Arg-Gly-Cys-amide (2.5 mg) was dissolved in 100 μL DMSO and added to the SPDP substituted particles, allowed to react at room temperature for 3 hours. The resulting nanoparticles of Formula V then were purified by gel filtration using 1×PBS as an eluant.

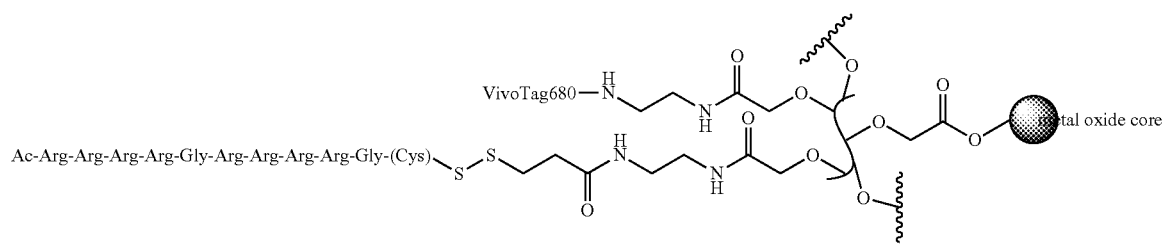

V

Example 6—Synthesis of Exemplary Fluorescent Metal Oxide Nanoparticle with Cyclic Peptide Biomolecule Amine functionalized fluorescent iron oxide nanoparticles described in Example 1 (600 μL of 2.5 mg/mL iron) were combined with 50 μL of 0.1 M HEPES, pH 7 and 4 mg of succinimidyl pyridinedithiopropionate (SPDP) in 100 μL DMSO and rotated for 5 hours at room temperature. The particles were separated from unreacted SPDP by gel filtration eluting with 0.1 M HEPES, pH 7.0. Cyclo(Arg-Gly-Asp-D-Phe-Cys) (1 mg) was dissolved in 100 μL DMSO and added to the SPDP conjugated particles, allowed to react at room temperature for 3 hours to produce the nanoparticles of Formula VI. The resulting nanoparticles were purified by gel filtration using 1×PBS as an eluant.

combined with 100 μL of 0.1 M HEPES, pH 7 and 3 mg of succinimidyl pyridinedithiopropionate (SPDP) in 250 μL DMSO and rotated for 2.5 hours at room temperature. The resulting particles were separated from unreacted SPDP by gel filtration using 0.1 M HEPES, pH 7.0 as an eluant. Gly-Pro-Leu-Gly-Val-Arg-Gly-Gly-Cys-amide (4 mg) was dissolved in 100 μL DMSO and added to the SPDP conjugated particles and allowed to react at room temperature for 10 hours, then purified by gel filtration using 0.1 M HEPES, pH 7 as an eluant. The solution was concentrated to 250 μL using a microconcentrator with a 50 kDa mwc membrane (Millipore). AlexaFluor750 (120 μL of 4.9 mM dye in DMF) then was added and the solution rotated at room temperature for 2 hours. The resulting nanoparticles of Formula VII then were purified by gel filtration using 1×PBS as an eluant.

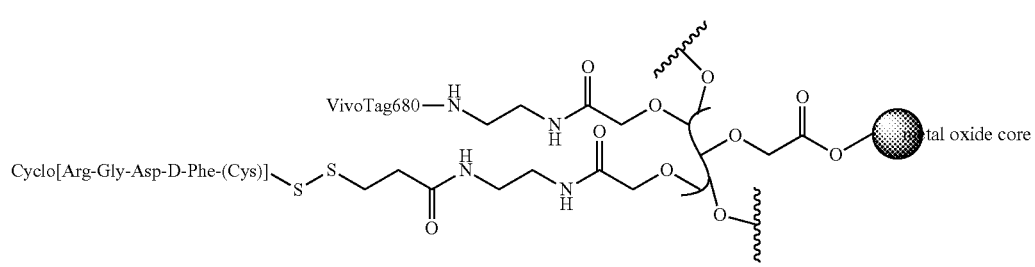

VI

Example 7—Synthesis of Exemplary Fluorescent Metal Oxide Nanoparticle with Activatable Biomolecule The amine functionalized iron oxide nanoparticles from Example 1 [see paragraph 150] (250 μL 88 mM Fe) were

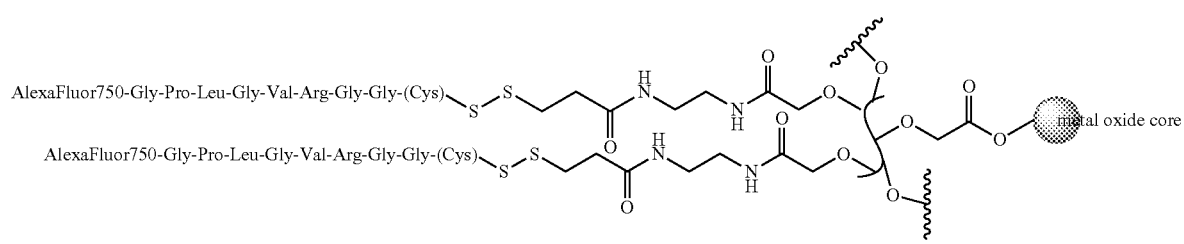

VII

Example 8—Synthesis of Exemplary Fluorescent Metal Oxide Nanoparticle with Biomolecule Compound Nanoparticles of Formula I from Example 1 (500 µL, 6.8 mg/mL iron) and 50 µL 0.1 M HEPES, pH 7, is combined with N,N-dipicolyl-gamma-aminobutyric acid NHS ester and allowed to react at room temperature overnight and then complexed with $Zn^{2+}$. The resulting particles are purified by gel filtration using Biorad Biogel P-60 eluting with 1×PBS to give nanoparticles of Formula VIII.

pH 7 and 4 mg of succinimidyl pyridinedithiopropionate (SPDP) in 100 µL DMSO and rotated for 5 hours at room temperature. The particles are separated from unreacted SPDP by gel filtration eluting with 0.1 M HEPES, pH 7.0. The N,N-dipicolylamine-peptide (1 mg) is dissolved in 100 µL DMSO and added to the SPDP conjugated particles, allowed to react at room temperature for 3 hours. The resulting nanoparticles of Formula IX then are purified by gel filtration eluting with 1×PBS and complexed with $Zn^{2+}$.

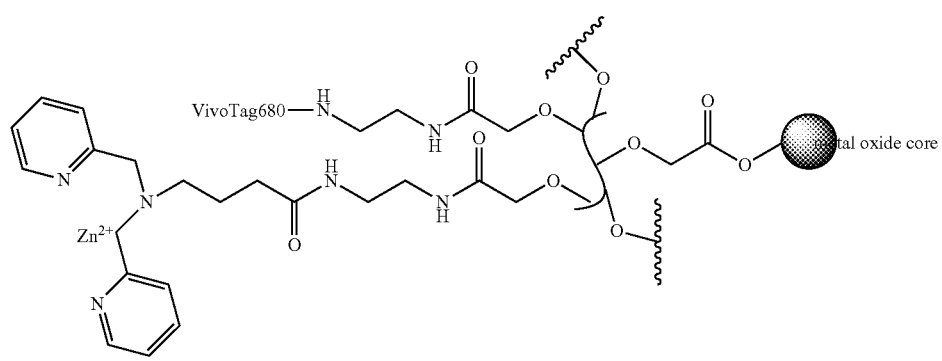

VIII

Example 9—Synthesis of Exemplary Fluorescent Metal Oxide Nanoparticle with Biomolecule Compound Nanoparticles of Formula I from Example 1 (600 µL of 2.5 mg/mL iron) is combined with 50 µL of 0.1 M HEPES,

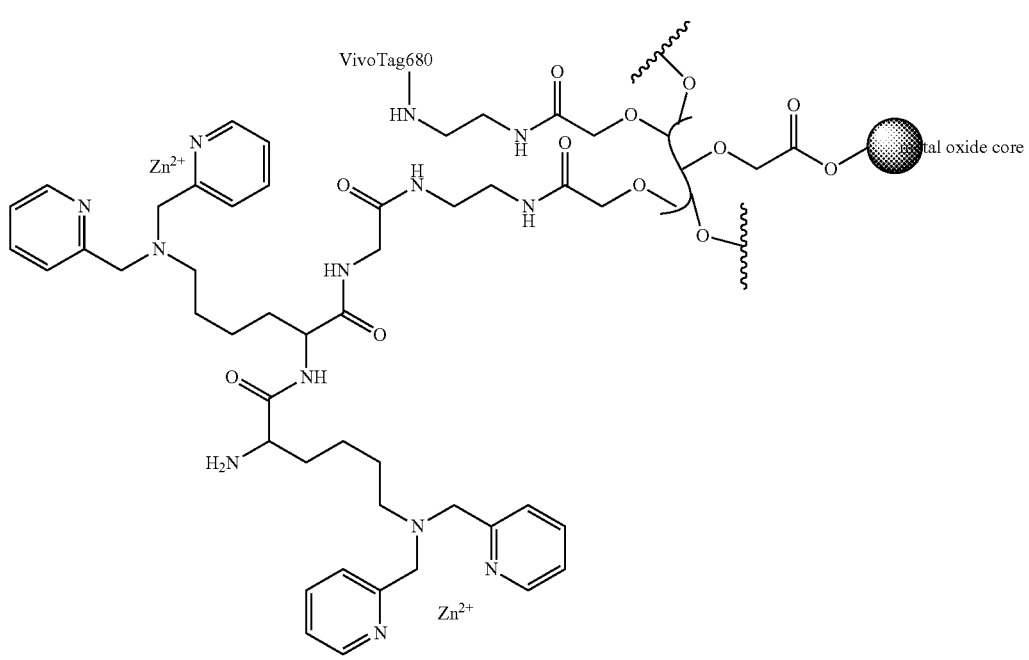

IX

Example 10—Synthesis of Exemplary Fluorescent Metal Oxide Nanoparticle with Peptide Biomolecule The amine functionalized fluorescent iron oxide nanoparticles described in Example 1 (600 µL of 2.5 mg/mL iron) are combined with 50 µL of 0.1 M HEPES, pH 7 and 4 mg of succinimidyl pyridinedithiopropionate (SPDP) in 100 µL DMSO and rotated for 5 hours at room temperature. The particles are separated from unreacted SPDP by gel filtration eluting with 0.1 M HEPES, pH 7.0. Val-His-Pro-Lys-Gln-His-Arg-Gly-Gly-Ser-Lys(FITC)-Gly-Cys-NH$_2$ (1 mg) is dissolved in 100 µL DMSO and added to the SPDP conjugated particles, allowed to react at room temperature for 3 hours. The resulting nanoparticles of Formula X then are purified by gel filtration eluting with 1×PBS.

The resulting carboxymethyl-polyvinylalcohol (37 g) was dissolved in 750 mL of hot (90° C.) water, filtered through a 0.7µ glass fiber filter (Whatman) and cooled to room temperature. Ferric chloride (4.65 mL of a 67% w/v solution, 20 mmol) was added slowly with stirring. The solution was transferred to a jacketed beaker with an overhead stirrer and cooled to 5° C. Ammonium hydroxide (20 mL of 33%, 390 mmol) was added via syringe drop by drop with vigorous stirring over 5 minutes. The temperature then was raised to 80° C. over 20 minutes and held at that temperature for 60 minutes. The solution was cooled, diluted with 400 mL deionized water and filtered successively through paper (3µ, Whatman), glass fiber (0.7µ, Whatman) and polyethersulfone (0.2 µl, Millipore) filters. The filtered solution then was dialyzed exhaustively using a 300 kDa mw cut-off hollow fiber cartridge and concentrated using a pressure filtration

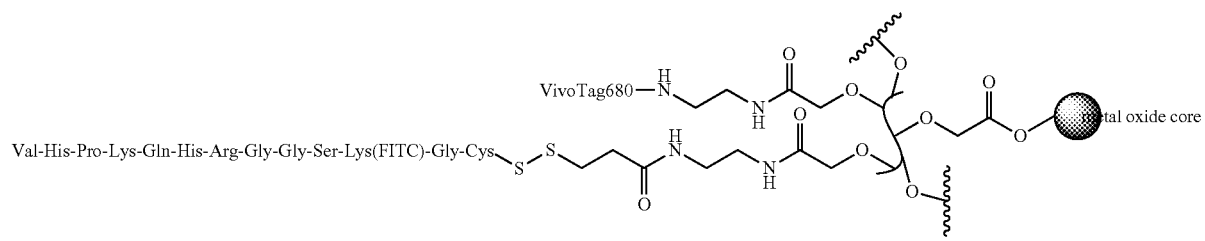

X

Example 11—Synthesis of Exemplary Fluorescent Ferric Oxide Nanoparticles

Polyvinyl alcohol (6 kDa, Polysciences, 30 g) was dissolved in 140 mL of water by heating to 90° C. The solution was cooled and transferred to a 500 mL jacketed beaker equilibrated to 15° C. 100 mL of 50% NaOH was added slowly with vigorous stirring using an overhead stirrer until a smooth, relatively homogeneous suspension formed. Bromoacetic acid (100 g) was dissolved in 50 mL of water and added slowly with vigorous stirring, making sure the temperature stayed below 35° C. After complete addition, the mixture was stirred for 15 hours at room temperature, and then neutralized with 6 M HCl to pH~7. Carboxymethyl-polyvinylalcohol was precipitated by addition of cold ethanol, filtered, washed with 70% ethanol, pure ethanol, and ether and then dried under vacuum. The carboxyl content (in µmol/g) of the polymer was determined by titration to neutrality of an acidified sample of the polymer. A range of 450-850 µmol/g was found, depending on the amount of bromoacetic acid used.

device to yield stable stock solutions of carboxylate functionalized ferric oxide nanoparticles.

To about 200 mL of the stock solution (~400 mg Fe), ethylene diamine hydrochloride (70 mL of a 2 M solution adjusted to pH 6.5 with sodium hydroxide) and N-(3-dimethyl-aminopropyl)-N'-ethyl carbodiimide (EDC) (4 g) were combined in a 500 mL flask and allowed to react overnight at room temperature. The solution was exhaustively dialyzed using a 300 kDa mwc hollow fiber cartridge and concentrated with a pressure filtration device to yield stable solutions of amine functionalized ferric oxide nanoparticles.

The resulting amine functionalized ferric oxide nanoparticles (4.8 mL, 88 mM Fe) from Example 1 were combined with 1.0 mL of 0.1 M HEPES, pH 7.0 and 250 µL of 3.75 mM VivoTag™680 NHS ester (VisEn Medical, Woburn, Mass.) in DMSO and allowed to react at room temperature for 4 hours and then separated from unreacted dye to yield nanoparticles of Formula XI.

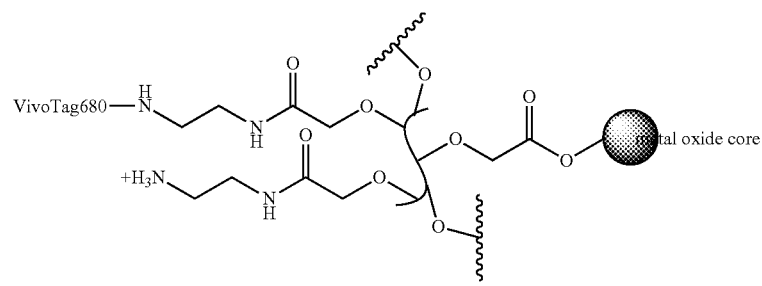

XI

Example 12—Synthesis of Exemplary Fluorescent Metal Oxide Nanoparticles with Alkyne Functionality 4-Pentynoic acid (59 mg, 0.6 mmol), disuccinimidyl carbonate (200 mg, 0.78 mmol) and N-methylmorpholine (73 µL, 0.66 mmol) were combined in 1.0 mL of DMF and allowed to react at room temperature for 2 hours. Then 33 µL of the activated alkyne solution was added to 1.5 mL of the amine functionalized fluorescent iron oxide nanoparticles described in Example 1 (6.25 mg/mL Fe) in 0.1 M HEPES, pH 7. The solution was rotated at room temperature for 4 hours and purified on P-60 gel using deinoized water as an eluant.

Example 13—Synthesis of Exemplary Fluorescent Metal Oxide Nanoparticles with VCAM-1 Peptide The amine functionalized fluorescent iron oxide nanoparticles described in Example 11 (625 µL of 4.84 mg/mL iron in 0.1 M HEPES, pH 7.0) and 30 µL of 44 mg/mL succinimidyl iodoacetate (SIA) in DMSO were combined and rotated for 2 hour. The particles were separated from unreacted SIA by gel filtration using Biorad Biogel P-60 using 20 mM HEPES, pH 7.0 as an eluant. 1.2 mg of the VCAM-1 peptide was added to the particles in 60 µL DMSO and the solution was rotated overnight. The resulting VCAM-1 labeled nanoparticles were purified by gel filtration using 1×PBS as an eluant.

Example 14—Comparison of the Nanoparticles of the Invention with CLIO Particles

This example shows that the nanoparticles of the invention are much brighter than the CLIO particles containing the same number of the same fluorochromes.

In this experiment, the amine functionalized particles of Example 1 (prior to the addition of fluorochromes) and amine-functionalized CLIO particles were used as starting materials. 50 µL aliquots, at an iron concentration of 6 mg/mL in 0.1 M HEPES, pH 7.0, were combined with a range from 1 µL to 30 µL of 5 mM fluorochrome (VivoTag680 or Cy5.5) stock solution in DMSO and allowed to react for 1 hour at room temperature. The labeled particles were purified from free fluorochrome by gel filtration.

The resulting particles were characterized to measure the number of reactive amines per particle, the number of amines available after attaching 40 VT680 dyes, the level of autoquenching with 40 VT680 dyes, the maximum fluorescence units per particle, and the maximum fluorescence units per iron atom. The results are summarized in TABLE 2.

In these analyses, iron content of the particle solutions was determined by digesting the iron core in 6 M HCl with 0.3% $H_2O_2$ at 50-60° C. for one hour and measuring the absorbance of the resulting $FeCl_3$ solution at 410 nm. An extinction coefficient of $\epsilon_{410}$=1370 $M^{-1}cm^{-1}$ was used for $FeCl_3$ in 6 M HCl. Fluorescence per particle was calculated by dividing the total fluorescence units measured by the concentration of iron and multiplying by 8000.

TABLE 2

| Features | Iron Oxide Nanoparticles | CLIO particles |
| --- | --- | --- |
| Number of reactive amines/particle | 200-300 | 50-60* |
| Amines available after attaching 40 VT680 dyes | 160-260 | 20 |
| Autoquenching with 40 VT680 | 0%-20% | ~60% |
| Maximum fluorescence units per particle | 100,000 | 20,000 |
| Maximum fluorescence units per iron atom | 12.5 | 2.5 |

Sun EY, Josephson L, Weissleder R.; Mol. Imaging. 2006 April-June; 5(2):122-8.

The larger number of reactive functional groups per particle, 200 to 300 for the fluorescent nanoparticles of the current invention versus 50 to 60 for CLIO permits coupling of many more fluorochromes (and without compromising reactive sites available for conjugating targeting molecules). In addition, the resulting nanoparticles of the invention experienced much lower autoquenching (0-20%) than the CLIO particles (~60%). The results, for example as summarized in Table 2, demonstrate that when similar numbers of fluorochromes are linked to the nanoparticles of the invention versus CLIO particles, the nanoparticles of the invention are significantly brighter than the CLIO particles.

FIG. 16 shows the total fluorescence per particle for fluorescent iron oxide nanoparticles of the invention and those made using the non-biodegradable cross-linked iron oxide (CLIO) nanoparticles loaded with varying amounts of either VivoTag680 or Cy5.5 fluorochromes (excitation was at 670 nm for VivoTag680 and 675 nm for Cy5.5). The quantity of dye loaded is expressed as the effective extinction coefficient ($\epsilon$) on a per particle basis.

At equivalent dye loadings (i.e., equivalent fluorochrome absorbance/iron concentration), fluorescent iron oxide nanoparticles of the present invention show significantly less autoquenching and higher fluorescence emission than CLIO particles of equal size for both Cy5.5 and VivoTag680 dyes. As shown in FIG. 16, the nanoparticles of the invention, for example, fluorescent iron oxide nanoparticles linked to VivoTag680 (■) or Cy5.5 (○) are much brighter than CLIO particles linked to VivoTag680 (x) or Cy5.5 (♦). As a consequence, the maximum achievable fluorescence per particle (the endpoints of each of the curves) is much higher for fluorescent iron oxide nanoparticles of the present invention than for CLIO particles—more than three times greater using VivoTag680 and more than four times greater using Cy5.5. In other words, the nanoparticles of the invention, therefore, are 3 times brighter than CLIO particles when labeled with VivoTag680 and 4 times brighter when labeled with Cy5.5.

Example 15—Imaging of Blood Vessels Using The Nanoparticles of Formula II

This example shows that the nanoparticles of the invention can image blood vessels in the ear of a mouse.

In this experiment, intravital confocal microscopy was performed using a Radiance 2100 system (Bio-Rad, Richmond, Calif.) equipped with four lasers, water immersion lenses and custom built heated stages for intravital imaging. Immediately prior to imaging, gas anesthetized animals received an intravenous injection of the nanoparticles of Formula II through the tail vein. Images of normal microvasculature of the ear were obtained. Signal intensity (SI) was recorded inside a vessel and a mono-exponential decay function was used to calculate the blood half-lives of the test article. The results are shown in FIG. 17.

The image in FIG. 17 demonstrates that the nanoparticles of Formula II can be used in intravital microscopy to image the blood vessels in the ear.

Example 16—Imaging of Tumors Using the Nanoparticles of Formula II

This example shows that the nanoparticles of the invention can be used to image tumors in vivo.

In this experiment, nude mice were injected in the first-second mammary fat pads with 3×10$^6$ human HT-29 colorectal cancer cells. One week later, when tumors were approximately 30 mm$^3$, the mice were injected intravenously with the nanoparticles of Formula II imaged 24 hours later on a Fluorescence Molecular Tomography system (VisEn Medical, Woburn Mass.). The results are shown in FIG. 18.

Figure 18:
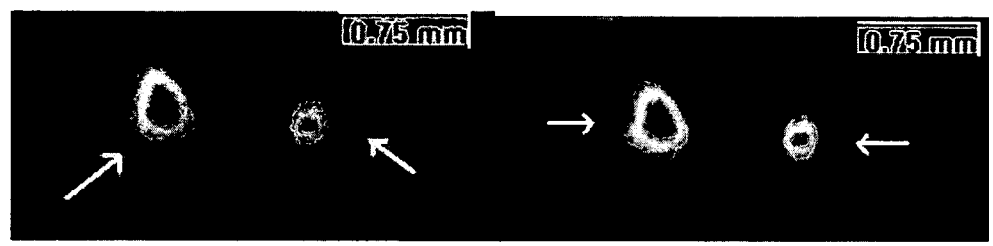
FIG. 18 is a picture showing images of human tumors in vivo in a mouse model using the nanoparticles described in Example 2 at 24 hours using fluorescence tomographic imaging.

The images in FIG. 18 demonstrate that the nanoparticles of Formula II can be used to image human tumors (shown by arrows) in a mouse model.

Example 17—Imaging of Arthritis Using the Nanoparticles of Formula II

This example shows that the nanoparticles of the invention can be used to image arthritis in vivo.

In this experiment, 5 week-old BALB/c mice were injected intravenously with 2 mg anti-collagen antibody mix (Chondrex) followed 3 days later by an intraperitoneal injection of lipopolysaccharide (50 μg, Chondrex). Four days later, when the mice exhibited marked arthritis in their hind paws (as assessed by paw thickness measurements using a caliper and clinical observation of edema/redness), the mice were injected intravenously with the nanoparticles of Formula II and imaged 24 hours later on a Fluorescence Molecular Tomography (V isEn Medical, Woburn Mass.). The results are shown in FIG. 19.

Figure 19:
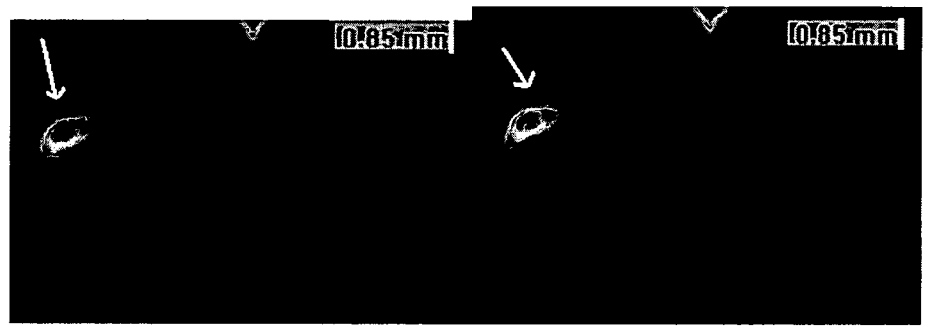
FIG. 19 is a picture showing images of arthritis in a mouse model using the nanoparticles described in Example 2 at 24 hours using fluorescent tomographic imaging.

The images in FIG. 19 demonstrate that the nanoparticles of Formula II can be used to image arthritis (shown by arrows) in a mouse model.

INCORPORATION BY REFERENCE

All publications, patents, and patent applications cited herein are hereby expressly incorporated by reference in their entirety and for all purposes to the same extent as if each was so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A fluorescent metal oxide nanoparticle comprising:
(a) a core comprising metal oxide;
(b) a non-crosslinked polycarboxyl polymer coating chemically linked to the core; and
(c) from about 10 to about 80 near infrared fluorochromes chemically linked to the coating, wherein (i) the nanoparticle has a molar extinction coefficient of about 1,500,000 $M^{-1}cm^{-1}$ to about 10,000,000 $M^{-1}cm^{-1}$, (ii) the fluorochromes emit fluorescent light upon illumination with light absorbable by the fluorochromes and (iii) the fluorochromes retain at least 50% of the fluorescence obtained from substantially the same number of free fluorochromes when measured under the same conditions.

2. The nanoparticle of claim 1, wherein the molar extinction coefficient is from about 2,000,000 $M^{-1}$ $cm^{-1}$ to about 5,000,000 $M^{-1}$ $cm^{-1}$.

3. The nanoparticle of claim 1, wherein the nanoparticle comprises from about 20 to about 60 fluorochromes chemically linked to the coating.

4. The nanoparticle of claim 1, wherein the nanoparticle retains from about 75% to about 95% of the fluorescence obtained from substantially the same number of free fluorochromes when measured under the same conditions.

5. The nanoparticle of claim 1, wherein the polymer is selected from the group consisting of a natural polymer, a synthetic polymer, and co-polymers thereof.

6. The nanoparticle of claim 1, wherein the polymer is carboxymethyl-polyvinylalcohol.

7. The nanoparticle of claim 1, wherein the coating is chemically linked to the core through a subset of the plurality of the carboxyl moieties.

8. The nanoparticle of claim 5, wherein the polymer comprises a plurality of reactive amines.

9. The nanoparticle of claim 8, wherein the nanoparticle comprises from about 100 to about 300 reactive amines per nanoparticle.

10. The nanoparticle of claim 9, wherein the nanoparticle comprises from about 150 to about 250 reactive amines per nanoparticle.

11. The nanoparticle of claim 8, wherein a fluorochrome is linked to the polymer via an amine moiety.

12. The nanoparticle of claim 6, wherein the carboxymethyl-PVA is linked to the fluorochrome through a diamine moiety represented by: $NH_2$—$(CH_2)_n$—$NH_2$, wherein n is an integer from 1 to 12.

13. The nanoparticle of claim 1, wherein a fluorochrome is linked to the polymer via a peptide linker.

14. The nanoparticle of claim 13, wherein the peptide comprises a protease cleavage site.

15. The nanoparticle of claim 1, wherein the metal oxide core is magnetic.

16. The nanoparticle of claim 1, wherein the metal oxide core is paramagnetic.

17. The nanoparticle of claim 16, wherein the metal oxide core is superparamagnetic.

18. The nanoparticle of claim 1, further comprising a biological modifier.

19. The nanoparticle of claim 18, wherein the biological modifier is polyethylene glycol or a derivative thereof.

20. The nanoparticle of claim 1, further comprising a biomolecule chemically linked to the polymer.

21. The nanoparticle of claim 20, wherein the biomolecule is covalently linked to the polymer through an amine moiety.

22. The nanoparticle of claim 20, wherein the biomolecule is a peptide, an antibody or an antigen binding fragment thereof, or a small molecule.

23. The nanoparticle of claim 20, wherein the biomolecule is a bivalent or multivalent binding molecule.

24. The nanoparticle of claim 20, wherein the biomolecule is an N,N-dipicolylamine moiety.

25. The nanoparticle of claim 20, wherein the biomolecule is protamine.

26. The nanoparticle of claim 20, wherein, when the biomolecule is a peptide, fluorescence of the nanoparticle increases once the peptide has been cleaved with an enzyme.

27. The nanoparticle of claim 20, comprising from about 1 to about 100 biomolecules chemically linked to the nanoparticle.

28. The nanoparticle of claim 20, further comprising a metal chelator chemically linked to the polymer.

29. The nanoparticle of claim 20, further comprising a radiolabel chemically linked to the polymer.

30. The nanoparticle of claim 20, further comprising a photosensitizer or phototherapy reagent chemically linked to the polymer.

31. The nanoparticle of claim 30, wherein the photosensitizer is porfimer sodium.

32. The nanoparticle of claim 31, wherein the nanoparticle has an absorption maxima and an emission maxima in the range from about 400 nm to about 1,200 nm.

33. The nanoparticle of claim 32, wherein the nanoparticle has an absorption maxima and an emission maxima in the range from about 600 nm to about 900 nm.

34. The nanoparticle of claim 1, wherein the fluorochrome is Cyanine 5, Cyanine 5.5 or Cyanine 7.

35. The nanoparticle of claim 34, wherein the nanoparticle has a diameter from about 10 nm to about 100 nm.

36. The nanoparticle of claim 34, wherein the nanoparticle is biocompatible.

* * * * *